(12) United States Patent
Yoshida et al.

(10) Patent No.: US 12,690,846 B2
(45) Date of Patent: Jul. 28, 2026

(54) MEDICAL IMAGE PROCESSING APPARATUS, X-RAY DIAGNOSTIC SYSTEM, AND NON-TRANSITORY COMPUTER-READABLE STORAGE MEDIUM STORING MEDICAL IMAGE PROCESSING PROGRAM

(71) Applicant: Canon Kabushiki Kaisha, Tokyo (JP)

(72) Inventors: Saki Yoshida, Shimoda (JP); Takuya Sakaguchi, Utsunoiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 101 days.

(21) Appl. No.: 18/458,263

(22) Filed: Aug. 30, 2023

(65) Prior Publication Data

US 2024/0074737 A1 Mar. 7, 2024

(30) Foreign Application Priority Data

Sep. 7, 2022 (JP) ................................. 2022-142553
Aug. 1, 2023 (JP) ................................. 2023-125592

(51) Int. Cl.
*A61B 8/00* (2006.01)
*A61B 6/00* (2006.01)
(Continued)

(52) U.S. Cl.
CPC .............. *A61B 8/5261* (2013.01); *A61B 6/12* (2013.01); *A61B 6/5247* (2013.01); *A61B 8/12* (2013.01)

(58) Field of Classification Search
CPC .................................................... A61B 8/5261
See application file for complete search history.

(56) References Cited

U.S. PATENT DOCUMENTS 8,961,420 B2 2/2015 Zhang
2007/0225553 A1* 9/2007 Shahidi .................. A61B 90/36
600/103

(Continued)

FOREIGN PATENT DOCUMENTS

JP 2020-5785 A 1/2020

OTHER PUBLICATIONS

Extended European Search Report Issued Jan. 22, 2024 in European Application 23195,477. 7, 6 pages.
(Continued)

*Primary Examiner* — Rochelle D Turchen
(74) *Attorney, Agent, or Firm* — Oblon, McClelland, Maier & Neustadt, L.L.P.

(57) ABSTRACT

In one embodiment, a medical image processing apparatus includes processing circuitry configured to: receive an ultrasonic image generated from a signal that is acquired by a detector of an ultrasonic catheter inserted into an object's body; receive an X-ray image depicting the detector and an imaging target that is at least one of a medical device inserted into the object's body and a region of interest inside the object's body; detect a position of the detector depicted in the X-ray image and a position of the imaging target depicted in at least one of the ultrasonic image and the X-ray image; and uses respective positions of the detector and the imaging target to calculate moving support information for moving the ultrasonic catheter in a manner such that the imaging target is included within a field of view "FOV" of the detector or moved towards the center of the FOV.

15 Claims, 18 Drawing Sheets

(51) Int. Cl.
   *A61B 6/12*       (2006.01)
   *A61B 8/12*       (2006.01)

(56)           References Cited

U.S. PATENT DOCUMENTS

2022/0409185 A1*   12/2022   Tanaka ................ G01S 7/52026
2024/0153113 A1*   5/2024   Gordon .................... G06T 7/74
2025/0040994 A1*   2/2025   Stopp .................... A61B 8/587

OTHER PUBLICATIONS

Kim, Young-Ho et al., "Automated Catheter Tip Repositioning for Intra-cardiac Echocardiography", Springer Nature 2021 Latex Template, Jan. 21, 2022, arXiv:2201.08889v1, 12 pages.

* cited by examiner

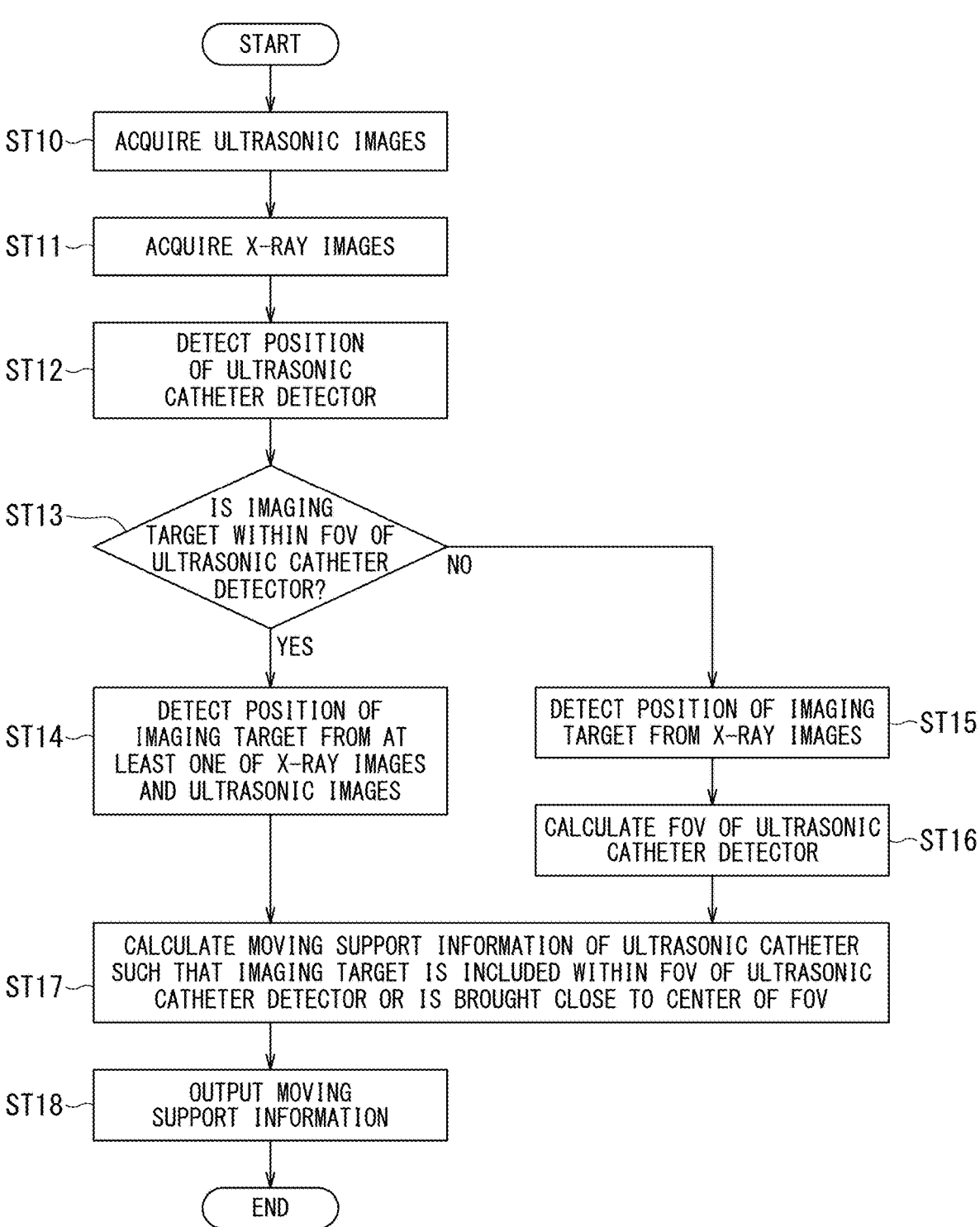

ST10 — ACQUIRE ULTRASONIC IMAGES

ST11 — ACQUIRE X-RAY IMAGES

ST12 — DETECT POSITION OF ULTRASONIC CATHETER DETECTOR

ST13 — IS IMAGING TARGET WITHIN FOV OF ULTRASONIC CATHETER DETECTOR?

NO

YES

ST14 — DETECT POSITION OF IMAGING TARGET FROM AT LEAST ONE OF X-RAY IMAGES AND ULTRASONIC IMAGES

ST15 — DETECT POSITION OF IMAGING TARGET FROM X-RAY IMAGES

ST16 — CALCULATE FOV OF ULTRASONIC CATHETER DETECTOR

ST17 — CALCULATE MOVING SUPPORT INFORMATION OF ULTRASONIC CATHETER SUCH THAT IMAGING TARGET IS INCLUDED WITHIN FOV OF ULTRASONIC CATHETER DETECTOR OR IS BROUGHT CLOSE TO CENTER OF FOV

ST18 — OUTPUT MOVING SUPPORT INFORMATION

FIG. 7

MEDICAL IMAGE PROCESSING APPARATUS, X-RAY DIAGNOSTIC SYSTEM, AND NON-TRANSITORY COMPUTER-READABLE STORAGE MEDIUM STORING MEDICAL IMAGE PROCESSING PROGRAM

CROSS-REFERENCE TO RELATED APPLICATION

This application claims the benefit of priority of Japanese Patent Application No. 2022-142553, filed on Sep. 7, 2022, and Japanese Patent Application No. 2023-125592, filed on Aug. 1, 2023, the entire contents of which are incorporated herein by reference.

TECHNICAL FIELD

Disclosed embodiments relate to a medical image processing apparatus, an X-ray diagnostic system, and a non-transitory computer-readable storage medium storing a medical image processing program.

BACKGROUND

Among medical image diagnostic apparatuses such as an X-ray diagnostic apparatus, an ultrasonic diagnostic apparatus, an X-ray CT (Computed Tomography) apparatus, and a magnetic resonance imaging apparatus, a plurality of medical image diagnostic apparatuses of different types are conventionally used in combination in some cases in order to improve accuracy and efficiency of treatment. For example, an X-ray diagnostic apparatus and an ultrasonic diagnostic apparatus are used in combination in IVR (Interventional Radiology) using a catheter.

An X-ray diagnostic apparatus is an apparatus that transmits X-rays through an object and visualizes the transmission image. For example, in the IVR using a catheter, a doctor inserts the catheter into the object while checking the position of the catheter in the blood vessel from fluoroscopic images or radiographic images time-sequentially generated by the X-ray diagnostic apparatus such as an X-ray angiography apparatus. After the catheter has progressed to the treatment target site (or diagnosis target site) of the object, ultrasonic images may be used in combination with X-ray images to depict tissues that are difficult to be checked from X-ray fluoroscopic images and radiographic images, such as soft tissues.

In catheter treatment of structural heart disease (SHD) such as left atrial appendage occlusion and observation of the anatomical structure and/or physiological function of the heart and large vessels, transesophageal echocardiography (TEE) is conventionally known to be useful. However, the TEE is an examination in which an ultrasonic endoscope is inserted from the mouth into the esophagus and the heart is observed from the esophagus, and thus, general anesthesia (i.e., full anesthesia) of the object is usually required. Contrastively, intracardiac echocardiography (ICE), which is one of the ultrasonic catheters with a built-in phased array element configured to transmit and receive ultrasonic waves at its tip, can be performed under local anesthesia and is less invasive than the TEE. Hence, attention has been focused on the ICE in combination with an X-ray diagnostic apparatus in SHD treatment, for example.

However, in general, the region of the ultrasonic image to be generated from the signals acquired by the ICE, i.e., the imaging region (hereinafter referred to as a FOV or field of view) in the ICE is narrower than that in the TEE. Thus, the lesion site which is the region of interest in the SHD treatment, such as the left atrial appendage, and the medical device, such as the left atrial appendage closure device, may be partially or entirely out of the FOV. When part or all of the region of interest is out of the FOV in the ICE, the manipulator needs to appropriately advance the ICE such that the region of interest is depicted within the FOV in the ICE.

Even when the treatment target site as the region of interest and/or the medical device are entirely depicted in part of the FOV in the ICE, it is a complicated task to: search the FOV in the ICE for a two-dimensional ultrasonic image by which the placement state of the medical device can be checked; and display such an image. Further, when part or all of the region of interest is not depicted in the FOV in the ICE, the manipulator searches for the two-dimensional ultrasonic image of the region of interest while performing manipulation in the ICE, which imposes a heavy burden on the manipulator.

In recent years, robots for supporting catheterization procedures have also been developed. These robots, i.e., robotic support systems are under development for the purpose of performing catheterization procedures from a remote location and/or performing fully automated or semi-automated catheterization procedures. In other words, a robot for supporting catheterization procedures may replace the above-described manipulator.

BRIEF DESCRIPTION OF THE DRAWINGS

In the accompanying drawings:

FIG. 7 is a flowchart illustrating processing to be executed by the medical image processing apparatus according to the first embodiment;

DETAILED DESCRIPTION

Hereinbelow, embodiments of a medical image processing apparatus, an X-ray diagnostic system, and a non-transitory computer-readable storage medium storing medical image processing program will be described in detail by referring to the accompanying drawings.

In one embodiment, a medical image processing apparatus includes processing circuitry configured to: receive an ultrasonic image generated from a signal that is acquired by a detector of an ultrasonic catheter inserted into a body of an object; receive an X-ray image in which the detector of the ultrasonic catheter and an imaging target are depicted, the imaging target being at least one of a medical device inserted into the body of the object and a region of interest inside the body of the object; detect (a) a position of the detector of the ultrasonic catheter depicted in the X-ray image and (b) a position of the imaging target depicted in at least one of the ultrasonic image and the X-ray image; and calculate moving support information based on the detected position of the detector of the ultrasonic catheter and the detected position of the medical device, the moving support information being for moving the ultrasonic catheter in such a manner that the imaging target is included within a field of view "FOV" of the detector or moved towards a center of the FOV of the detector.

First Embodiment

Figure 1:
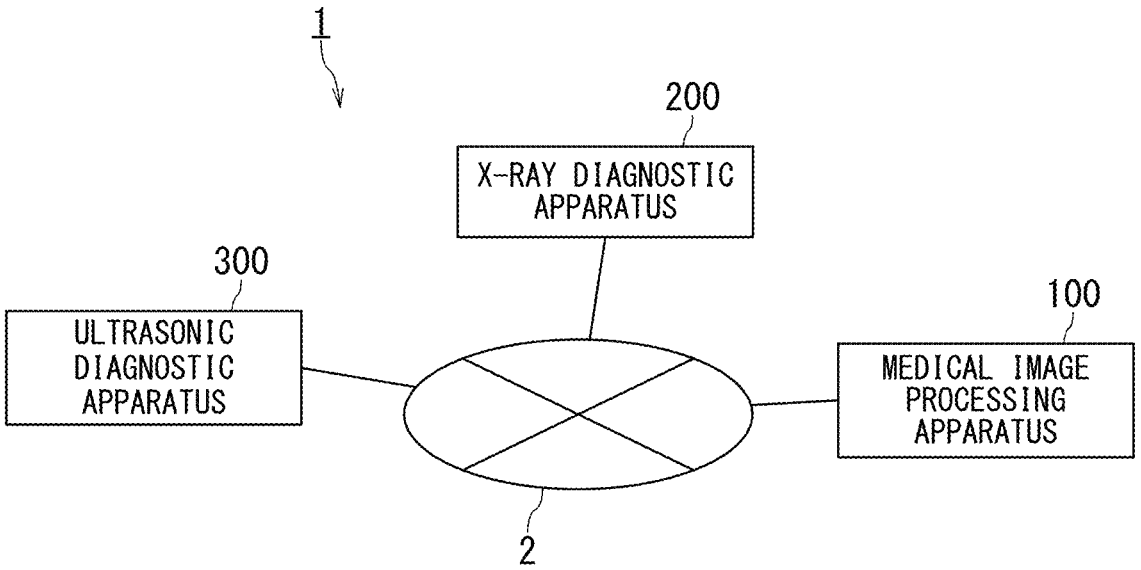
FIG. 1 is a first schematic diagram illustrating a configuration of an X-ray diagnostic system provided with a medical image processing apparatus according to the first embodiment.

FIG. 1 is a first schematic diagram illustrating a configuration of an X-ray diagnostic system 1 provided with a medical image processing apparatus according to the first embodiment. As shown in FIG. 1, the X-ray diagnostic system 1 includes a medical image processing apparatus 100 and an X-ray diagnostic apparatus 200, for example. The medical image processing apparatus 100 and the X-ray diagnostic apparatus 200 are interconnected via a network 2. Furthermore, the network 2 is connected to an ultrasonic diagnostic apparatus 300.

Figure 2:
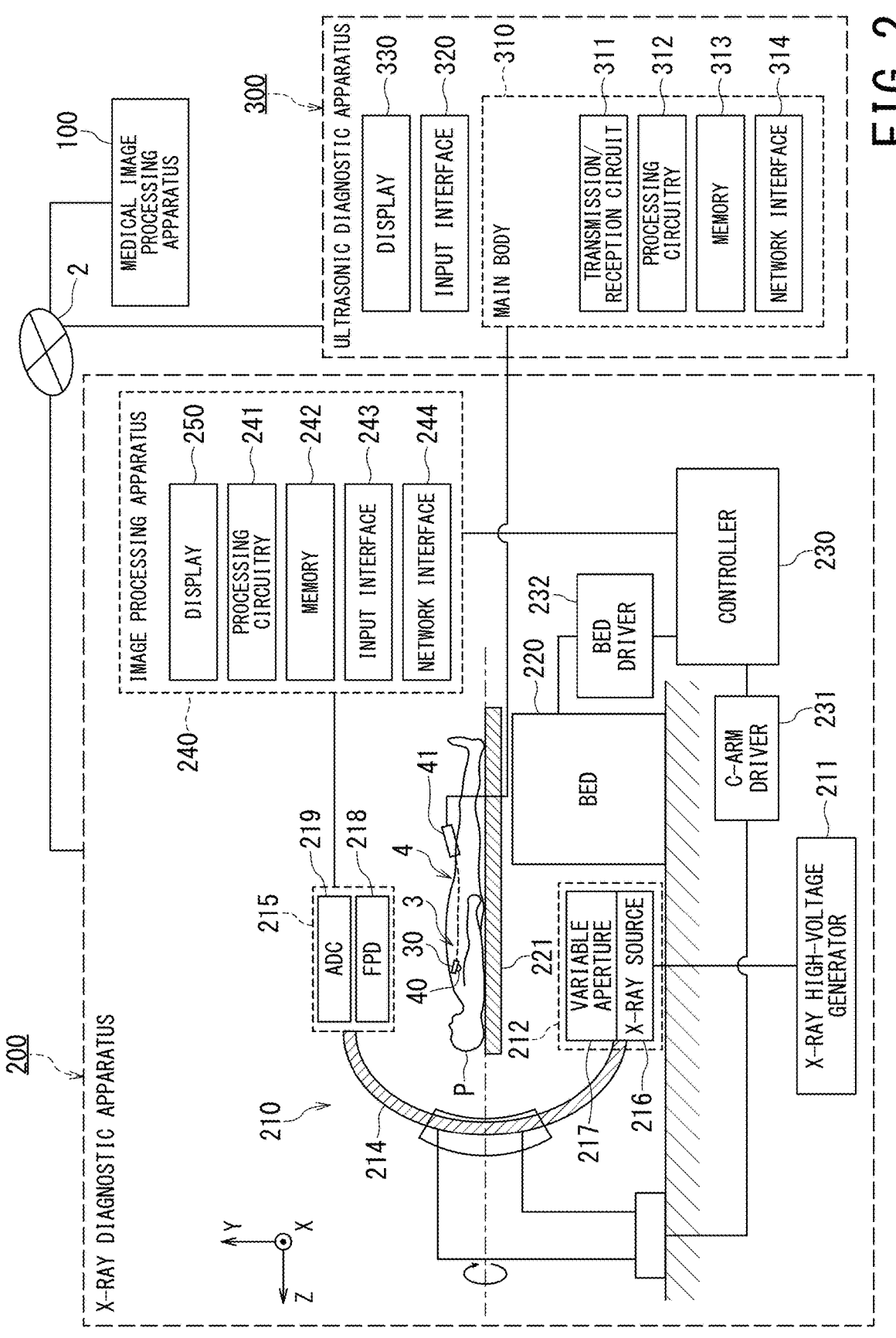
FIG. 2 is a second schematic diagram illustrating a configuration of the X-ray diagnostic system provided with the medical image processing apparatus according to the first embodiment.

FIG. 2 is a second schematic diagram illustrating a configuration of the X-ray diagnostic system 1 provided with the medical image processing apparatus 100 according to the first embodiment. FIG. 2 illustrates a configuration of the X-ray diagnostic apparatus 200 according to the first embodiment and the ultrasonic diagnostic apparatus 300 connected to the X-ray diagnostic system 1.

As shown in FIG. 2, the X-ray diagnostic apparatus 200 according to the first embodiment includes a scanner 210, a bed 220, a controller 230, an image processing apparatus 240. The scanner 210, the bed 220, and the controller 230 are generally installed in an operating room (which may be an examination room or a treatment room), and the image processing apparatus 240 is installed in a control room adjacent to the operating room.

The scanner 210 includes: an X-ray high-voltage generator 211; an X-ray irradiator 212; a table 221 (i.e., catheter table) 221; a C-arm 214; an X-ray detector 215; a C-arm driver 231; and a bed driver 232.

The X-ray irradiator 212 is installed at one end of the C-arm 214. The X-ray irradiator 212 is provided so as to be able to move back and forth under the control of the controller 230. The X-ray irradiator 212 has an X-ray source 216 (for example, an X-ray tube) and a variable aperture 217. The X-ray tube receives high voltage power from the X-ray high-voltage generator 211 and generates X-rays depending on the conditions of high voltage power. The variable aperture 217 movably supports the aperture blades made of an X-ray shielding material at the X-ray irradiation port of the X-ray tube. Note that a radiation quality adjusting filter for adjusting the quality of the X-rays generated by the X-ray tube may be provided on the front face of the X-ray tube.

The X-ray detector 215 is provided at the other end of the C-arm 214 so as to face the X-ray irradiator 212. The X-ray detector 215 is provided so as to be able to move back and forth under the control of the controller 230. The X-ray detector 215 includes a flat panel detector (FPD) 218 and an analog to digital converter (ADC) 219.

The FPD 218 has a plurality of detection elements arranged in two dimensions. The scanning lines and signal lines are arranged so as to be orthogonal to each other between the respective detection elements of the FPD 218. Note that a grid may be provided on the front of the FPD 218.

The ADC 219 converts projection data of the time-sequential analog signals (i.e., video signals) outputted from the FPD 218 into digital signals, and outputs the digital signals to the image processing apparatus 240.

The X-ray irradiator 212 and the X-ray detector 215 are held by the C-arm 214 so as to face each other with the object interposed as the center therebetween. Under the control of the controller 230, the C-arm 214 integrally moves the X-ray irradiator 212 and the X-ray detector 215 in the arc direction of the C-arm 214 by the C-arm driver 231. Although a description will be given of a configuration in which the X-ray diagnostic apparatus 200 includes the C-arm 214 and the C-arm 214 integrally drives or works the X-ray irradiator 212 and the X-ray detector 215, embodiments of the present invention are not limited to such a configuration. For example, the X-ray diagnostic apparatus 200 may be configured to individually drive both the X-ray irradiator 212 and the X-ray detector 215 without including the C-arm 214 such that both (212 and 215) are independent of each other.

Although FIG. 2 illustrate a configuration of a single-plane X-ray diagnostic apparatus 200 having only one C-arm, it may be configured as a biplane X-ray diagnostic apparatus 200 that can perform fluoroscopic imaging from two directions at the same time by using two C-arms.

The bed 220 is supported by the floor and supports the table 221. The bed 220 can slide the table 221 in each of the X-axis and Z-axis directions, move the table 221 up and down (i.e., in the Y-axis direction), and rotate the table 221 under the control of the controller 230. Although a description will be given of an under-tube system in which the X-ray irradiator 212 is disposed below the table 221 in the scanner 210, the scanner 210 may be configured as an over-tube system in which the X-ray irradiator 212 is disposed above the table 221.

The controller 230 includes a central processing unit (CPU, not shown) and a memory (not shown). Under the control of the image processing apparatus 240, the controller 230 controls driving of the bed 220 as well as driving of the X-ray irradiator 212, the X-ray detector 215, and the C-arm 214 of the scanner 210 for alignment, i.e., for positioning. Under the control of the image processing apparatus 240, the controller 230 also controls driving of the X-ray irradiator 212, the X-ray detector 215, and the C-arm driver 231 so as to perform X-ray fluoroscopic imaging and/or X-ray radiographic imaging for manipulation of a medical device.

The image processing apparatus 240 is computer-based and includes: processing circuitry 241, a memory 242, an input interface 243, a network interface 244, and a display 250.

The processing circuitry 241 includes a special-purpose or general-purpose processor and is a circuit configured to control driving of the entire X-ray diagnostic apparatus 200 by, for example, software processing in which the processor executes various programs stored in the memory 242. The processing circuitry 241 controls the controller 230 based on: input from a user via the input interface 243; execution of the various programs; and various data. In addition, the processing circuitry 241 controls the entire X-ray diagnostic apparatus 200 so as to: generate X-ray images (i.e., fluoroscopic images and/or radiographic images) of the object P based on the signals acquired by the scanner 210; and display X-ray images stored in the memory 242 on the display 250, for example.

The memory 242 stores: various programs for controlling the controller 230 and executing various processing such as image processing and display processing; various data such as diagnostic information and diagnostic protocols; and image data, for example. The memory 242 is configured as, for example, a semiconductor memory device such as a RAM (Random Access Memory) and a flash memory, a hard disk, or an optical disk.

The network interface 244 is an interface for performing wired or wireless communication with various apparatuses connected to the network 2. For example, the X-ray diagnostic apparatus 200 can exchange various data and images with various apparatuses including the medical image processing apparatus 100 and the ultrasonic diagnostic apparatus 300 via the network interface 244.

The input interface 243 includes: at least one input device that can be manipulated by a user; and an input circuit to which signals from the input device are inputted. The input device includes: a mouse; a keyboard; a touch pad by which input manipulation is achieved by touching its manipulation screen; a touch screen in which the display screen and the touch pad are integrated; a non-contact input circuit using an optical sensor; and a voice input circuit, for example.

The display 250 displays: a GUI for receiving user's instructions via the input interface 243; and X-ray images generated by the image processing apparatus 240, for example. The display 250 also displays various messages and display information in order to notify the user of the processing status and processing results of the X-ray diagnostic apparatus 200. Further, the display 250 may include a speaker and be able to output the above-described information items as sound. The display 250 can also display various support images and support information that are generated by the medical image processing apparatus 100 for supporting a medical procedure such as a catheterization procedure, including data and images received from various apparatuses connected to the network 2.

As shown in FIG. 2, the ultrasonic diagnostic apparatus 300 includes a main body 310, an input interface 320, and a display 330. The ultrasonic diagnostic apparatus 300 further includes an ultrasonic catheter 3 that is communicably connected to the main body 310.

The main body 310 is computer-based and includes: a transmission/reception circuit 311; processing circuitry 312; a memory 313, and a network interface 314.

The transmission/reception circuit 311 outputs ultrasonic drive signals to the ultrasonic catheter 3 and generates reflected wave data from reflected wave signals received by the ultrasonic catheter 3.

The processing circuitry 312 includes a special-purpose or general-purpose processor and is a circuit configured to control driving of the entire ultrasonic diagnostic apparatus 300 by, for example, software processing in which the processor executes various programs stored in the memory 313. The processing circuitry 312 controls the processing of the transmission/reception circuit 311 based on: input from a user via the input interface 320; execution of the various programs having been read from the memory 313; and various data. In addition, the processing circuitry 312 generates ultrasonic image data based on the reflected wave signals received by the ultrasonic catheter 3, and generates ultrasonic images for display from the generated ultrasonic image data. Further, the processing circuitry 241 controls the entire ultrasonic diagnostic apparatus 300 so as to display ultrasonic images stored in the memory 312 on the display 330, for example.

The memory 313 stores: various programs for transmitting/receiving ultrasonic waves and for executing image processing and display processing; various data such as diagnostic information and diagnostic protocols; reflected wave data; and image data, for example. The memory 313 is configured as, for example, a semiconductor memory device such as a RAM and a flash memory, a hard disk, or an optical disk.

The network interface 314 is an interface for performing wired or wireless communication with various apparatuses connected to the network 2. For example, the ultrasonic diagnostic apparatus 300 can exchange various data with various apparatuses including the medical image processing apparatus 100 and the X-ray diagnostic apparatus 200 via the network interface 314.

The input interface 320 includes: at least one input device that can be manipulated by a user; and an input circuit to which signals from the input device are inputted. The input device includes: a mouse; a keyboard; a touch pad by which input manipulation is achieved by touching its manipulation screen; a touch screen in which the display screen and the touch pad are integrated; a non-contact input circuit using an optical sensor; and a voice input circuit, for example.

The display 330 displays: a GUI for receiving user's instructions via the input interface 320; and ultrasonic images generated by the main body 310, for example. The display 330 also displays various messages and display information in order to notify the user of the processing status and processing results of the main body 310. Further, the display 220 may include a speaker and be able to output the above-described information items as sound. The display 330 can also display various support images and support information that are generated by the medical image processing apparatus 100 for supporting a medical procedure such as a catheterization procedure, including data and images received from various apparatuses connected to the network 2.

FIG. 2 also illustrate an ultrasonic catheter 3 to be used for a catheterization procedure. In this specification, mainly, an ultrasonic probe that is communicably connected to the main body 310 and is inserted into the heart chamber of the object P is referred to as the ultrasonic catheter 3. The ultrasonic catheter 3 includes, for example, the ICE that is inserted into a body cavity from the femoral vein so as to be advanced into the heart and can scan anatomical sites such as the left atrium, the left atrial appendage, the aorta, the mitral valve, and the aortic valve so as to generate an ultrasonic image. Aside from the ICE, a device to be inserted into a tubular tissue such as a blood vessel of the object P for scanning anatomical sites such as the tubular tissue and generating an ultrasonic image may be used as the ultrasonic catheter 3.

Figure 9:
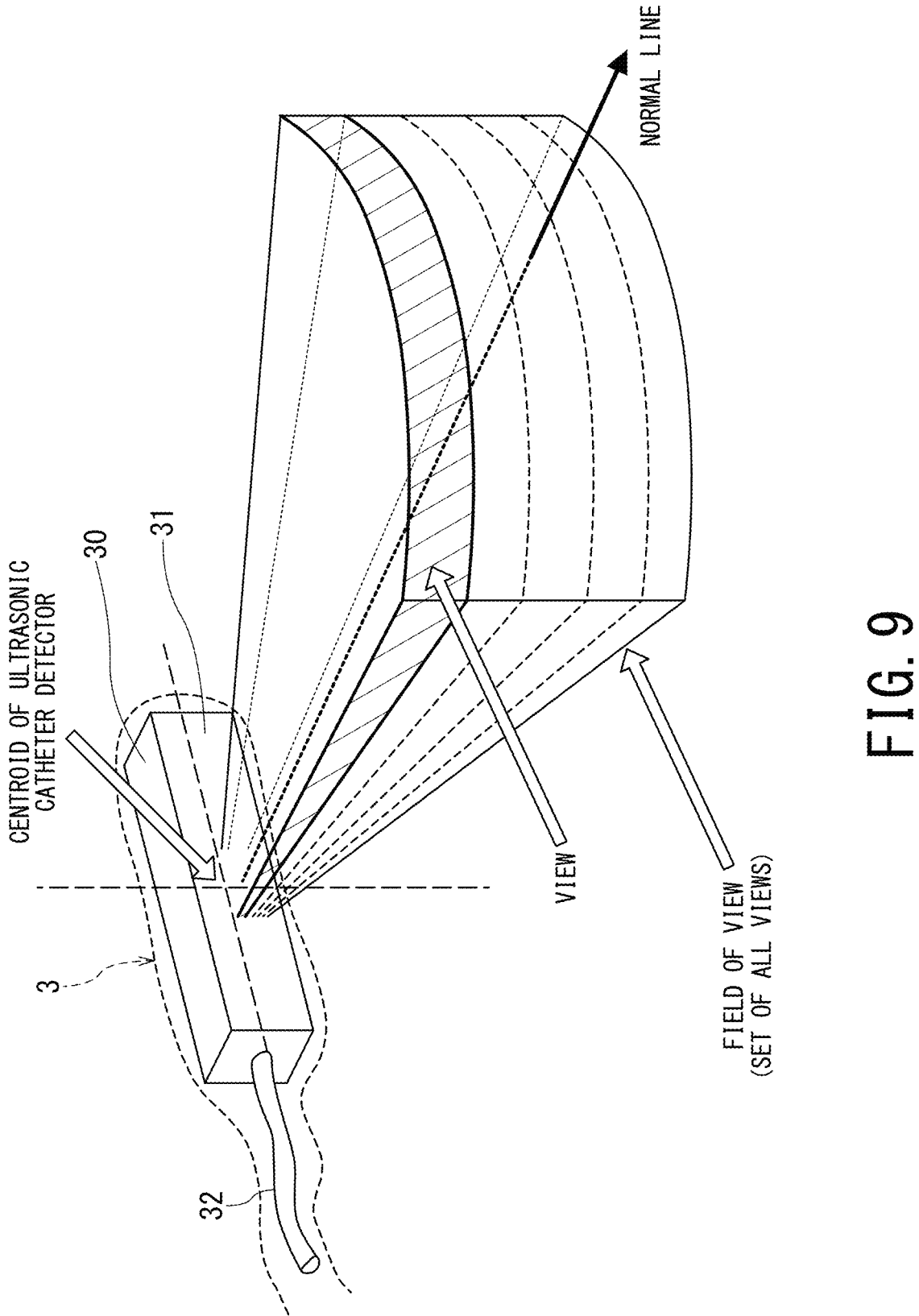
FIG. 9 is a schematic diagram illustrating positional information of an ultrasonic detector and a FOV in an ultrasonic image according to the first embodiment.

The ultrasonic catheter 3 is inserted into the body cavity of the object P and manipulated inside the body cavity. As shown in FIG. 9, the ultrasonic catheter 3 has a detector at its tip, and an array plane 31 of the detector 30 has a plurality of piezoelectric elements (i.e., transducers). The plurality of piezoelectric elements generate ultrasonic waves based on the drive signals inputted from the main body 310 through the cable 32, receive the reflected waves from the object P, and convert them into electrical signals. The array plane 31 is a two-dimensional array that can scan a three-dimensional space. Additionally, the array plane 31 may be a one-dimensional array that can scan a two-dimensional space.

FIG. 2 also illustrates a manipulation catheter 4 according to the first embodiment to be used for a catheterization procedure. In this specification, the term "manipulation catheter 4" mainly means a thin medical device that is inserted into the body cavity of the object P and/or tubular tissue such as a blood vessel so as to be used for treatment, diagnosis, or support in treatment (i.e., treatment process). The manipulation catheter 4 includes: a thin tube called a catheter; a guide wire for guiding the catheter to the treatment target site; and a medical device 40 attached to the tip of the catheter, for example.

The device-manipulating tool 41 is a device that is manipulated by a manipulator such as a doctor for inserting the manipulation catheter 4 into the blood vessel of the object P and advancing it to a predetermined target site. Here, the predetermined target site is a site where treatment, diagnosis, or support in the treatment process is performed, and can also be called a region of interest inside the body of the object P.

The medical device 40 is a member to be used at the predetermined target site where treatment is performed after the manipulation catheter 4 is inserted into the body of the object P. Aspects of the medical device 40 include devices such as an occlusive device, a balloon, and a stent (for example, the medical device 40a in FIG. 5).

The medical device 40 may also be a member that is used at a predetermined target site during a treatment process after the manipulation catheter 4 is inserted into the body of the object P. The medical device 40 may be a puncture needle (e.g., the medical device 40b in FIG. 4), for example.

Note that one manipulation catheter 4 may be provided with a plurality of medical devices 40.

Figure 3:
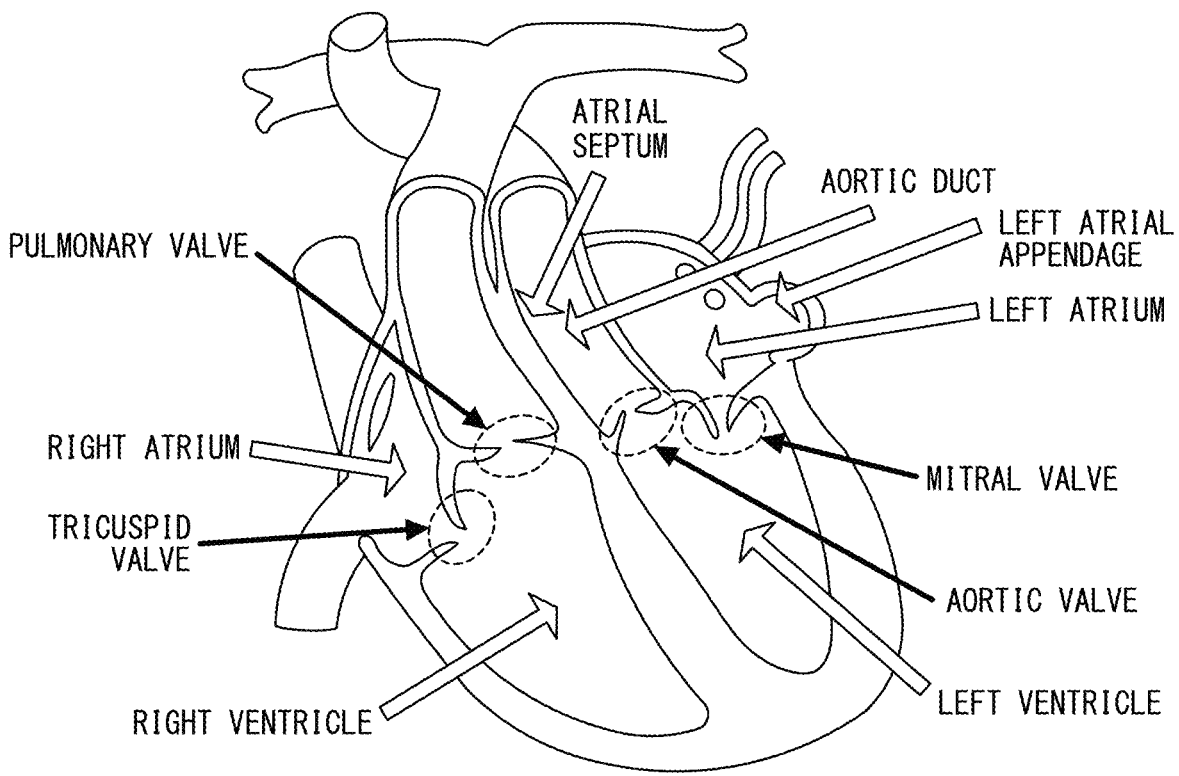
FIG. 3 is a schematic diagram illustrating a surgical site according to the first embodiment.
Figure 4:
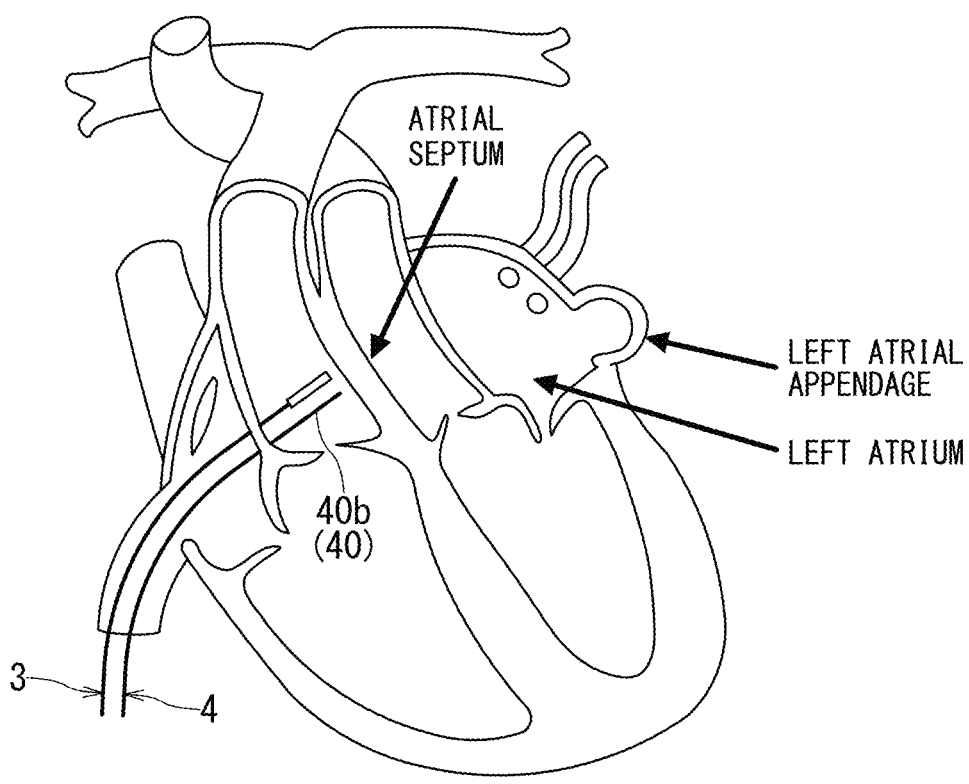
FIG. 4 is a first schematic diagram illustrating a catheterization procedure according to the first embodiment.
Figure 5:
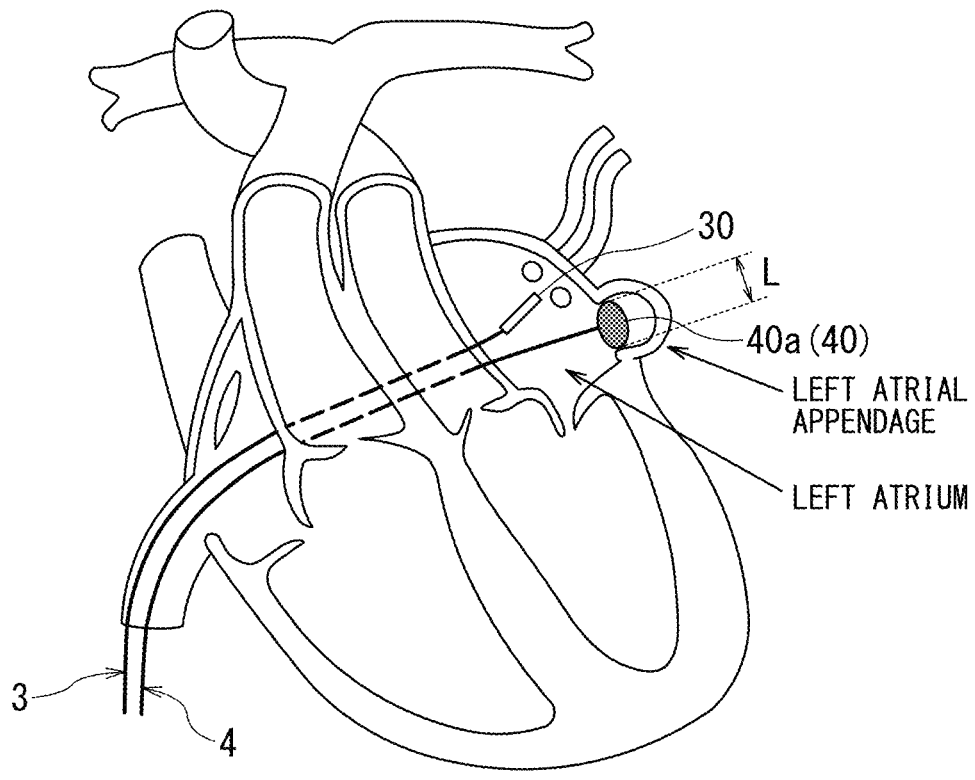
FIG. 5 is a second schematic diagram illustrating a catheterization procedure according to the first embodiment.

FIG. 3 is a schematic diagram illustrating a surgical site according to the first embodiment, and FIG. 4 and FIG. 5 are schematic diagrams illustrating septal puncture and a left atrial appendage closure procedure that is one case of catheterization procedures according to the first embodiment. In the left atrial appendage closure procedure in general, after the ultrasonic catheter 3 and the manipulation catheter 4 are inserted into the body of the object P through the blood vessels, both are advanced to the right atrium, the left atrium, and then the vicinity of the left atrial appendage, which is a treatment target site.

Specifically, as shown in FIG. 4, the septal puncture is performed in order to advance the ultrasonic catheter 3 and the manipulation catheter 4 to the vicinity of the left atrial appendage, which is the treatment target site. The septal puncture is medical treatment in which the atrial septum is punctured with a needle during the treatment process. The manipulator observes either or both the medical device 40b and the predetermined target site to be treated during the treatment process. For this purpose, the manipulator manipulates both the ultrasonic catheter 3 and the manipulation catheter 4 so as to advance the ultrasonic catheter 3 to a position where both the medical device 40 and the target site to be treated in the treatment process are satisfactorily depicted. For example, in the septal puncture, the vicinity of the atrial septum is observed as a region of interest inside the body of the object P by using the ultrasonic catheter 3.

Subsequently, after the septal puncture as shown in FIG. 5, firstly, the size of the left atrial appendage, which is the treatment target site, is measured by using the ultrasonic catheter 3 to determine the size of the occlusion device.

Secondly, an occlusion device appropriate for the size of the left atrial appendage is navigated to the left atrium.

Thirdly, in order to observe the shape of the left atrial appendage on the X-ray image immediately before placement of the occlusion device, a contrast medium is administered.

Fourthly, the occlusion device at the tip of the manipulation catheter 4 is deployed and placed there such that the left atrial appendage is occluded. In this fourth stage, the manipulator observes the conditions of the treatment target site, such as contact between the left atrial appendage and the occlusion device. Depending on the observation, the manipulator performs measures such as re-placement of the occlusion device.

In other words, in the fourth stage, in order to observe either or both the medical device 40 and the (predetermined) treatment target site, the manipulator manipulates both the ultrasonic catheter 3 and the manipulation catheter 4 so as to advance the ultrasonic catheter 3 to a position at which both the medical device 40 and the treatment target site are satisfactorily depicted in time-sequential display images in real time. For example, in the left atrial appendage closure procedure, the vicinity of the left atrial appendage is observed as a region of interest inside the body of the object P by using the ultrasonic catheter 3.

Although the left atrial appendage closure procedure and the occlusion device are described as one case of catheterization procedures according to the first embodiment in FIG. 3 to FIG. 5, the present embodiment can also be applied to an arbitrary medical action in the treatment process and other intracardiac procedures aside from the left atrial appendage closure procedure, as exemplified by ASD (atrial septal defect) closure, a mitral valve closure procedure, and BAV (Balloon Aortic Valvuloplasty). In addition, the present embodiment can also be applied to other medical devices 40 aside from the puncture needle and the occlusion device. Although a description has been given of the medical treatment and the treatment process using the medical device 40 as one case of catheterization procedures according to the first embodiment, the present embodiment can also be used for other applications of the medical device 40, such as diagnosis by the medical device 40.

Figure 6:
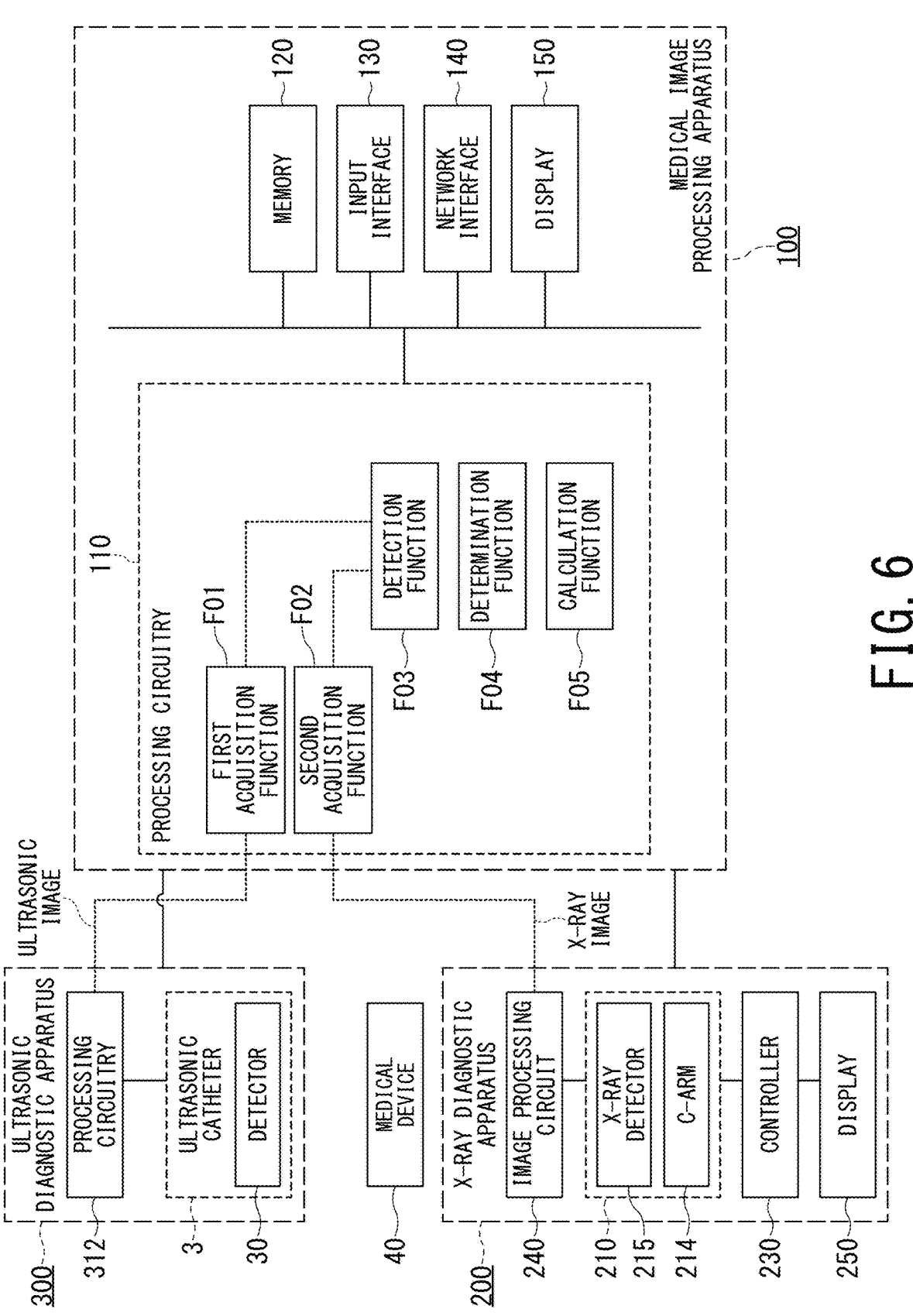
FIG. 6 is a schematic diagram illustrating a configuration of the medical image processing apparatus according to the first embodiment.

FIG. 6 illustrates a configuration of the medical image processing apparatus 100 according to the first embodiment. As shown in FIG. 6, the medical image processing apparatus 100 according to the first embodiment is connectable to the X-ray diagnostic apparatus 200 and the ultrasonic diagnostic apparatus 300, and is configured as a computer such as a workstation and a personal computer. The medical image processing apparatus 100 provides the manipulator with images and information for supporting a medical procedure such as a catheterization procedure.

The medical image processing apparatus 100 includes at least: processing circuitry 110; a memory 120; an input interface 130; and a network interface 140.

The medical image processing apparatus 100 may further include a display 150. The display 150 provides the manipulator with moving support information of the ultrasonic catheter 3 generated by the medical image processing apparatus 100. The display 150 may be, for example, a large display device to be placed at a position where the manipulator can easily see it. The display 150 may include a speaker and be able to output the moving support information as sound. In addition, the display 150 can also display: data generated by the processing circuitry 110 including the moving support information; various images generated by the medical image processing apparatus 100 for supporting a medical procedure such as a catheterization procedure; and data and images received from various apparatuses connected via the network 2.

The network interface 140 is an interface for performing wired or wireless communication with various apparatuses connected to the network 2. For example, the medical image processing apparatus 100 can exchange various data and images with various apparatuses including the X-ray diagnostic apparatus 200 and the ultrasonic diagnostic apparatus 300 via the network interface 140.

The input interface 130 includes: at least one input device that can be manipulated by the user; and an input circuit to which signals from the input device are inputted. The input device includes: a mouse; a keyboard; a touch pad by which input manipulation is achieved by touching its manipulation screen; a touch screen in which the display screen and the touch pad are integrated; a non-contact input circuit using an optical sensor; and a voice input circuit, for example.

The memory 120 is configured as a recording component such as a semiconductor memory element including a random access memory (RAM) and a flash memory, a hard disk, and an optical disc. The memory 120 stores various processing programs (including an OS (Operating System) in addition to an application program) to be used in the processing circuitry 110 and data necessary for executing the programs. Further, the memory 120 can store various data such as image data inputted via the input interface 130 and/or the network interface 140.

The processing circuitry 110 includes a special-purpose or general-purpose processor and implements various functions described below by software processing in which the programs stored in the memory 120 are executed. The processing circuitry 110 implements each of a first acquisition function F01, a second acquisition function F02, a detection function F03, a determination function F04, and a calculation function F05.

Each of these functions will be described by using the flowchart of FIG. 7 and schematic diagrams of FIG. 8 to FIG. 11B. FIG. 7 is a flowchart illustrating processing to be executed by the medical image processing apparatus 100 and/or the medical image processing program according to the first embodiment.

In the step ST10, ultrasonic images generated from the signals acquired by the ultrasonic diagnostic apparatus 300 are acquired by the detector 30 of the ultrasonic catheter 3 inserted into the body of the object P to be diagnosed or treated. The processing of acquiring the ultrasonic images of the object P in the step ST10 is performed by the first acquisition function F01.

In the step ST11, X-ray images, which are generated by causing the X-ray diagnostic apparatus 200 to image the object P to be diagnosed or treated, are acquired. The X-ray images to be acquired in the step ST11 are X-ray images, each of which depicts: the detector 30 of the ultrasonic catheter 3; and the imaging target. In the following description, the term "imaging target" means at least one of the medical device inserted into the body of the object P and the region of interest in the body of the object P, unless otherwise specifically noted.

Figure 8:
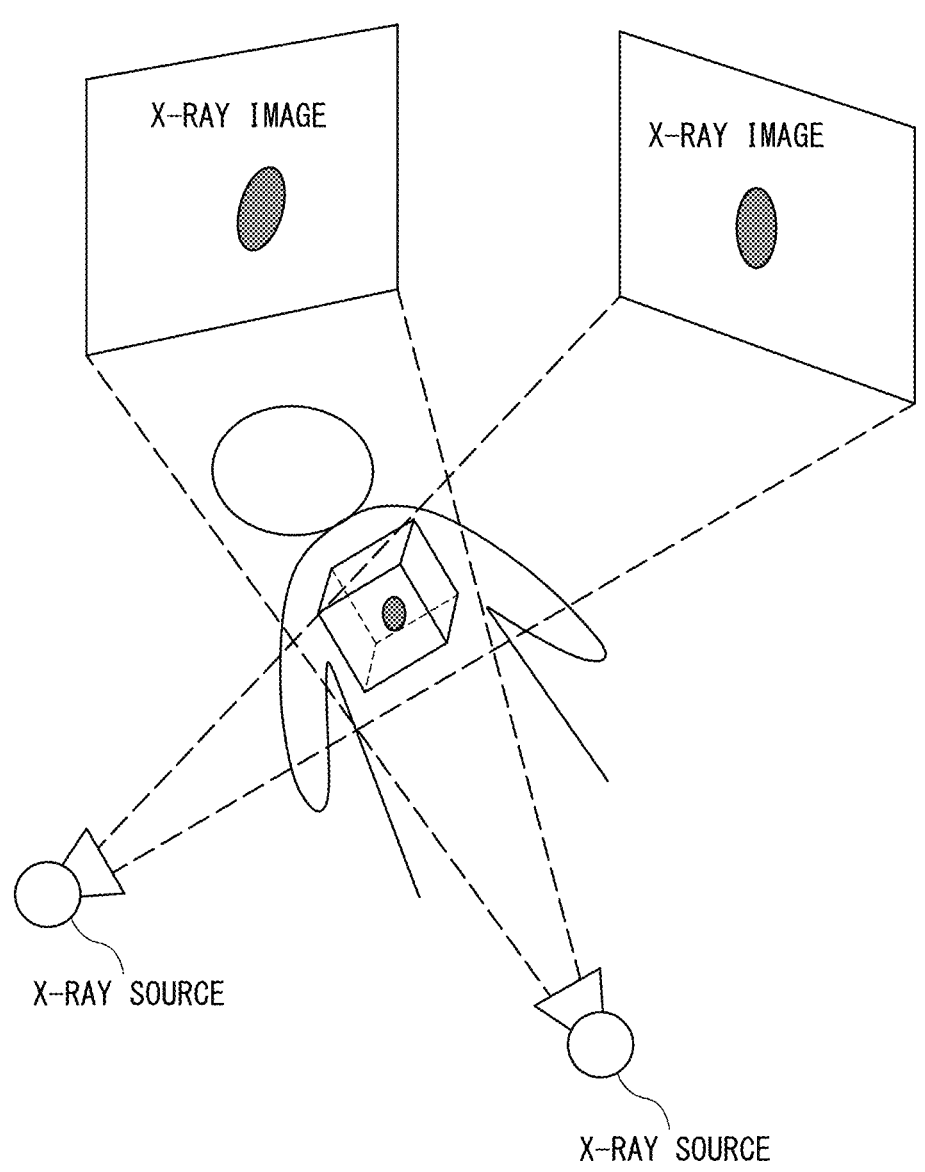
FIG. 8 is a schematic diagram illustrating X-ray imaging according to the first embodiment.

FIG. 8 is a schematic diagram illustrating X-ray imaging according to the first embodiment. As shown in FIG. 8, the X-ray images in the step ST11 are radiographic images (still images) or time-sequential fluoroscopic images (moving images), which are generated by irradiating the object P with X-rays from at least two directions to include the same part of the object P. The processing of acquiring the X-ray image data of the object P in the step ST11 is performed by the second acquisition function F02.

In the step ST12, the position of the detector 30 of the ultrasonic catheter 3 depicted in the X-ray images acquired in the step ST11 is detected. The position of the detector 30 of the ultrasonic catheter 3 in, for example, the X-ray coordinate system is specified from the plurality of X-ray images depicting the same site of the object P acquired in the step ST11 by using a known technique such as the principle of a stereo camera. The processing of detecting the position of the detector 30 of the ultrasonic catheter 3 in the step ST12 is performed by the detection function F03.

Here, the X-ray coordinate system is defined as a right-handed coordinate system in which the three body axes of the object P are used as the three axes of the coordinate system as follows: the right-left (i.e., lateral) direction is the X-axis; the anterior-posterior direction is the Y-axis; and the head-foot direction is the Z axis, as shown in FIG. 2.

FIG. 9 is a schematic diagram illustrating positional informational of the ultrasonic detector and the FOV in each ultrasonic image according to the first embodiment. As shown in FIG. 9, the positional information of the detector 30 of the ultrasonic catheter 3 includes: the position of the centroid (i.e., center of gravity) of the detector 30 of the ultrasonic catheter 3 in the X-ray coordinate system; and the normal vector of the array plane 31 of the detector 30 extending from the position of the centroid, for example.

In FIG. 9, the array plane 31 of the detector 30 of the ultrasonic catheter 3 is a two-dimensional array. In this specification, under the state where the position of the detector 30 of the ultrasonic catheter 3 and the angle of the array plane 31 of the detector 30 are fixed, each of a plurality of fan-shaped two-dimensional ultrasonic images generated from the acquired ultrasonic data is referred to as a "view".

Further, the range corresponding to the three-dimensional ultrasonic image in which the plurality of views are superimposed over the entire range, i.e., the range corresponding to the set (or integration) of all the views is referred to as an "FOV" or a field of view.

The FOV can be calculated if the scanning range of the detector 30 is determined under the state where the position of the detector 30 of the ultrasonic catheter 3 and the angle of the array plane 31 of the detector 30 are fixed.

Returning to FIG. 7, in the step ST13, the ultrasonic images acquired in the step ST10 are used to determine whether the imaging target including at least one of the medical device 40 and the region of interest inside the body of the object P is within the FOV of the detector 30 of the ultrasonic catheter 3 or not. Specifically, if the imaging target including at least one of the medical device 40 and the region of interest inside the body of the object P is depicted in the ultrasonic images acquired in the step ST10, it is determined that the imaging target is within the FOV of the detector 30. If the imaging target including at least one of the medical device 40 and the region of interest inside the body of the object P is not depicted in the ultrasonic images acquired in the step ST10, it is determined that the imaging target is not within the FOV of the detector 30. The processing of determining whether the imaging target is within the FOV of the detector 30 of the ultrasonic catheter 3 in the step ST13 is performed by the determination function F04.

Also when the "FOV" is composed of only one "view", i.e., when the FOV of the detector 30 is two-dimensional, the determination function F04 can perform the determination in the step ST13 as to whether the imaging target is within the FOV of the detector 30 of the ultrasonic catheter 3.

The processing of the step ST14 is performed if the determination in the step ST13 is YES, i.e., if all or part of the imaging target including at least one of the medical device 40 and the region of interest inside the body of the object P is within the FOV of the detector 30 of the ultrasonic catheter 3. In the step ST14, the position of the imaging target including at least one of the medical device 40 and the region of interest inside the body of the object P is detected from at least one of: the ultrasonic images acquired in the step ST10; and the X-ray images acquired in the step ST11. The processing of detecting the position of the imaging target in the step ST14 is performed by the detection function F03.

In the step ST14, in the case of detecting the position of the medical device 40 from the ultrasonic images acquired in the step ST10, the position of the centroid of the medical device 40 in the X-ray coordinate system is detected from the position of the medical device 40 depicted in the ultrasonic images, for example, from the position of the medical device in the FOV.

Regarding detection or estimation of the position of the centroid, a description will be given of the case where the medical device 40 depicted in the ultrasonic images does not include its centroid, for example, the case where only the edge of the medical device 40 is depicted in the ultrasonic images, by referring to the medical device 40a in FIG. 5. As shown in FIG. 5, the position of the centroid of the medical device 40a (40) in the X-ray coordinate system may be estimated from: the size of the treatment target site that can be equal to the diameter L of the medical device 40a (40); and the shape of the medical device 40 after its deployment (such as a sphere, an oval sphere, a doughnut, and a cylindrical shape). In the estimation of the size of the treatment target site, the measurement data for determining the size of the medical device 40a (40) can be used, and the X-ray images generated for checking the shape of the treatment target site immediately before placement of the medical device 40a (40) can also be used, for example.

In the step ST14, in the case of detecting the position of the imaging target (which is at least one of the medical device 40 and the region of interest inside the body of the object P) from the X-ray images acquired in the step ST11, the position of the centroid in the X-ray coordinate system for the imaging target may be detected from the plurality of X-ray images acquired in the step ST11 by using, for example, the principle of a stereo camera.

The processing of the step ST15 is performed if the determination in the step ST13 is NO, i.e., if the imaging target including at least one of the medical device 40 and the region of interest inside the body of the object P is not within the FOV of the detector 30 of the ultrasonic catheter 3. In the step ST15, the position of the imaging target (which is at least one of the medical device 40 depicted in the X-ray images acquired in the step ST11 and the region of interest inside the body of the object P) is detected. The position of the centroid in the X-ray coordinate system for the imaging target (which is at least one of the medical device 40 and the region of interest inside the body of the object P) is detected as the position of the imaging target from the plurality of X-ray images acquired in the step ST11 by using, for example, the principle of a stereo camera. The processing of detecting the position of the imaging target in the step ST15 is performed by the detection function F03.

In the step ST16, the FOV of the detector 30 is calculated from: the centroid of the array plane 31 constituting the detector 30 (i.e., the position of the detector 30 of the ultrasonic catheter 3 detected in the step ST12); the normal vector calculated from the orientation of the array plane 31; and the predetermined scanning range (i.e., known scanning range) of the detector 30. As shown in FIG. 9, the FOV of the detector 30 can be calculated from the scanning range of detector 30 under the state where the position of the detector 30 of the ultrasonic catheter 3 and the angle of the array plane 31 of the detector 30 are fixed. The processing of calculating the FOV of the detector 30 of the ultrasonic catheter 3 in the step ST16 is performed by the calculation function F05.

In the step ST17, on the basis of: the position of the detector 30 of the ultrasonic catheter 3; and the position of the imaging target including at least one of the medical device 40 and the region of interest inside the body of the object P, the calculation function F05 calculates the moving support information for: moving the ultrasonic catheter 3; and thereby making the imaging target included within the FOV of the detector 30 of the ultrasonic catheter 3. Additionally or alternatively, on the basis of: the position of the detector of the ultrasonic catheter 3; and the position of the imaging target, the calculation function F05 calculates the moving support information for: moving the ultrasonic catheter 3; and thereby bringing the imaging target close to the center of the FOV of the detector 30 of the ultrasonic catheter 3.

Figures 10A, 10B:
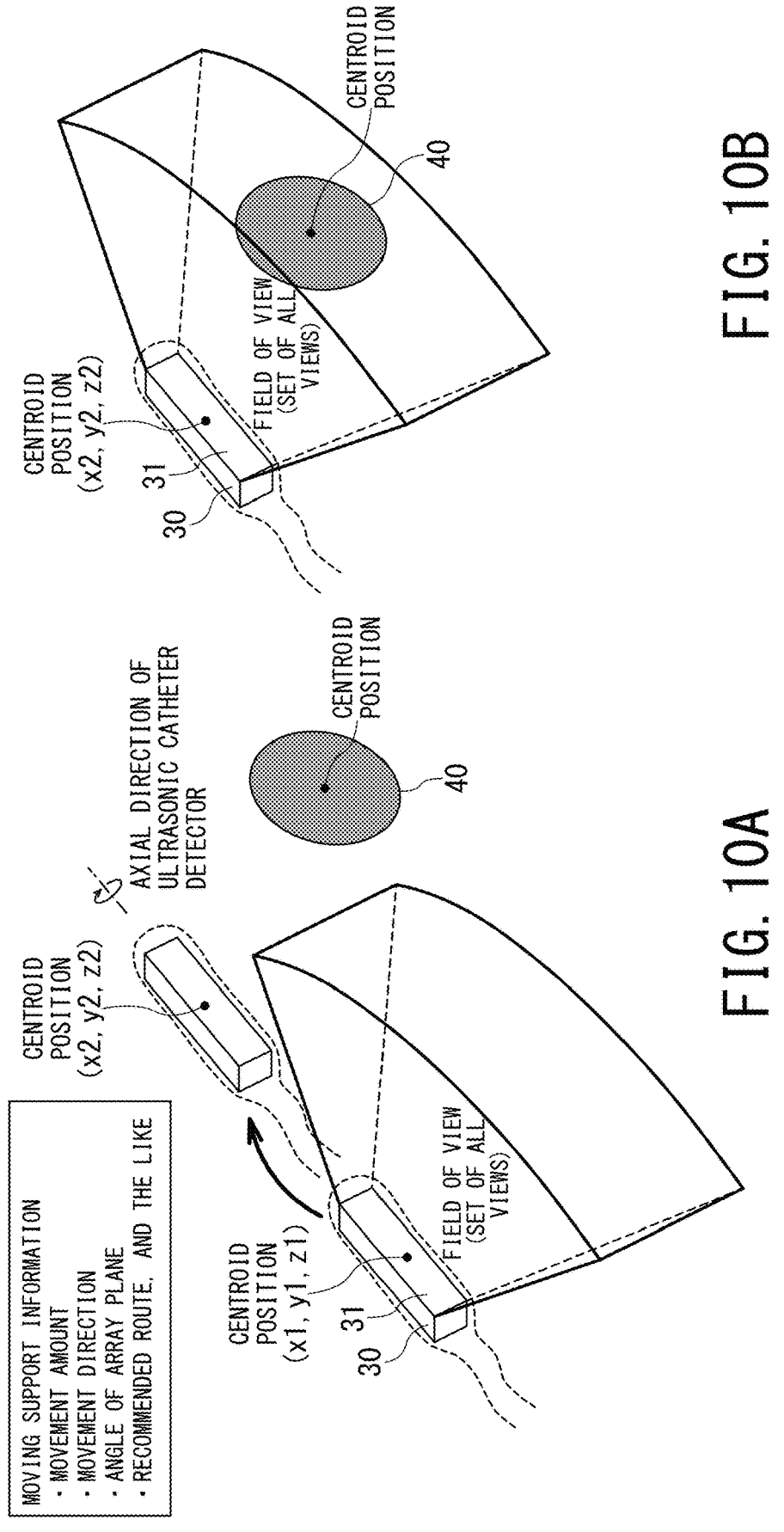
FIG. 10A and FIG. 10B are perspective views for illustrating movement support of the ultrasonic catheter in the first embodiment when a medical device is entirely out of the FOV of the detector of the ultrasonic catheter, and respectively correspond to before and after the movement support.
Figures 11A, 11B:
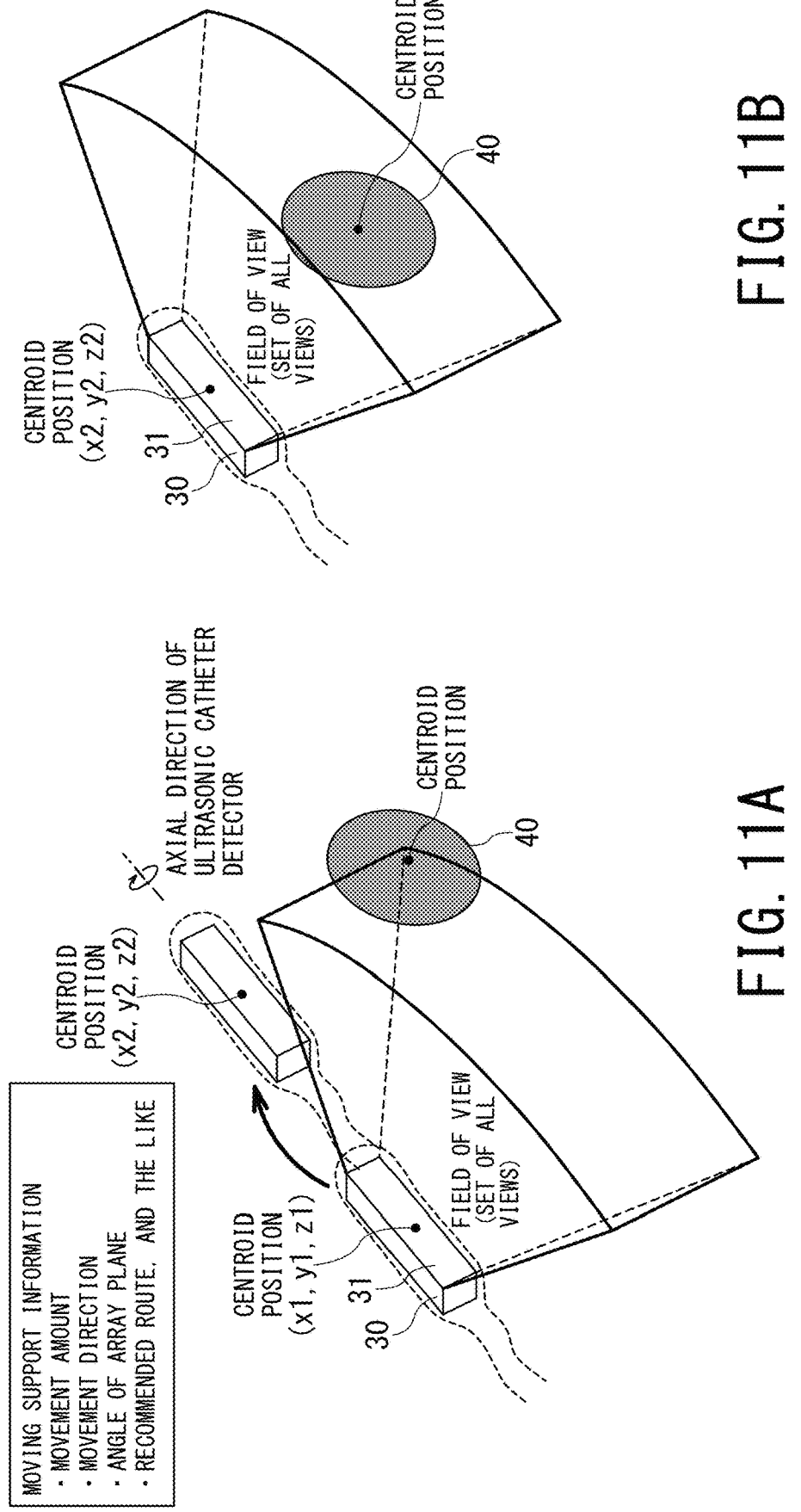
FIG. 11A and FIG. 11B are perspective views for illustrating movement support of the ultrasonic catheter in the first embodiment when the medical device is partially out of the FOV of the detector of the ultrasonic catheter, and respectively correspond to before and after the movement support.

FIG. 10A to FIG. 11B are perspective views for illustrating movement support of the ultrasonic catheter 3. In detail, FIG. 10A and FIG. 10B are for the case where the medical device 40 according to the first embodiment is entirely out of the FOV of the detector 30 of the ultrasonic catheter 3, and respectively correspond to before and after the movement support. Conversely, FIG. 11A and FIG. 11B are for the case where the medical device 40 according to the first embodiment is partially out of the FOV of the detector 30 of the ultrasonic catheter 3, and respectively correspond to before and after the movement support.

Hereinafter, the processing of the step ST17 will be described by referring to FIG. 10A to FIG. 11B for the case where the imaging target is the medical device 40. However, the imaging target is not limited to the medical device 40. The imaging target may be the region of interest inside the body of the object. The imaging target may include both the medical device 40 and the region of interest inside the body of the object. In these imaging targets, the movement of the ultrasonic catheter 3 can also be supported when part or all of the imaging target is out of the FOV of the detector 30 of the ultrasound catheter 3.

As shown in FIG. 10A and FIG. 11A, in the step ST17, when the medical device 40 is entirely or partially out of the FOV of the detector 30 of the ultrasonic catheter 3, the calculation function F05 calculates: executable movement amount by which the ultrasonic catheter 3 can advance; an executable moving direction of the ultrasonic catheter 3; and/or the angle of the array plane 31 of the detector 30, such that the medical device 40 is included within the FOV of the detector 30 of the ultrasonic catheter 3 or approaches the center of the FOV of the detector 30 of the ultrasonic catheter 3. In this specification, the movement amount may be either advance amount or retreat amount, and the moving direction may be either the direction of advancing (i.e., forward direction) or the direction of retreating (i.e., backward direction).

In the step ST17, also when the medical device 40 is moved from the state where the entire medical device 40 is within the FOV of the detector 30 of the ultrasonic catheter 3, the calculation function F05 can calculate the movement amount and moving direction of the ultrasonic catheter 3 and/or the angle of the array plane 31 of the detector 30, so that part or all of the medical device 40 does not deviate from the FOV of the detector 30 of the ultrasonic catheter 3.

As shown in FIG. 10A and FIG. 11A, the movement amount and moving direction of the ultrasonic catheter 3 are, for example, the amount and direction by which the position of the centroid of the detector 30 of the ultrasonic catheter 3 in the X-ray coordinate system is moved from the position (x1, y1, z1) to the position (x2, y2, z2). The angle of the array plane 31 of detector 30 is the amount to be rotated around the axis of detector 30.

When part or all of the medical device 40 is not within the FOV of the detector 30 of the ultrasonic catheter 3, the overlap between the FOV of the detector 30 and the entirety of the medical device 40 in the three-dimensional space can be calculated by assuming: the position of the centroid of the medical device 40 in the X-ray coordinate system, which is acquired in the step ST14 or ST15; the size of the treatment target site that can be equal to the diameter of the medical device 40; and the shape of the medical device 40 after its deployment, for example. From the calculated overlap between both, the calculation function F05 can calculate the movement amount and moving direction of the ultrasonic catheter 3 and the angle of the array plane 31 of the detector 30, which are required to overlap the entirety of the medical device 40 on the FOV of the detector 30 in the three-dimensional space.

The movement amount and moving direction of the ultrasonic catheter 3 and the angle of the array plane 31 of the detector 30 are preferably such that the entirety of the medical device 40 is maximally included within the FOV of the detector 30 of the ultrasonic catheter 3. In this specification, "to be maximally included" means the state in which the entirety of the medical device 40 is within the FOV of the detector 30 of the ultrasonic catheter 3 and is depicted as large as possible within the FOV of the detector in the ultrasonic image.

When part of the medical device 40 is within the FOV of the detector 30 of the ultrasonic catheter 3, the moving direction of the ultrasonic catheter 3 may be determined depending on which view of the plurality of ultrasonic images acquired the in step ST10 depicts the medical device 40. For example, when the FOV of the detector 30 of the ultrasonic catheter 3 is composed of a range of ten views from the view V1 to the view V10 and the medical device 40 is depicted only in the view V1 and the view V2, under the assumption that the medical device 40 is outside the FOV of the detector 30 on the side of the view V1, the moving direction of the ultrasonic catheter 3 may be determined as the direction in which the view V2, the view V1, and the outside of the FOV of the detector 30 on the side of the view V1 can eventually be depicted.

In addition, the moving support information of the ultrasonic catheter 3 may include: information for determining the appropriate moving speed of the ultrasonic catheter 3 suitable for the tissue or organ of the object P at the tip of the ultrasonic catheter 3; and information on a recommended route by which the ultrasonic catheter 3 can be moved at the determined moving speed and/or can be moved so as to bypass the tissue and/or organ of the object P without contacting them.

Returning to FIG. 7, in the step ST18, the moving support information of the ultrasonic catheter 3 calculated in the step ST17 is outputted. The moving support information of the ultrasonic catheter 3 is outputted to the display 150 and displayed on the display 150. Further, the moving support information of the ultrasonic catheter 3 may be outputted to at least one of the display 250 provided in the X-ray diagnostic apparatus 200 and the display 330 provided in the ultrasonic diagnostic apparatus 300 so as to be displayed on the display(s).

The output of the moving support information of the ultrasonic catheter 3 to be outputted to the display 150 includes at least one of information items of the moving support information calculated in the step ST17.

Since the moving support information of the ultrasonic catheter 3 is provided to the manipulator, the frequency of manipulations of the ultrasonic catheter 3 is reduced, and it is expected to improve the workflow so that the manipulator can concentrate on the manipulation of the manipulation catheter 4.

In the first embodiment, the steps ST10 to ST12 may be performed in any order as long as the step ST12 is performed after the step ST11. The execution order of these three steps is not limited to the order of the step ST10, step ST11, and step ST12 but may be the order of step ST11, step ST12, and step ST10 or the order of step ST11, step ST10, and step ST12.

First Modification of First Embodiment

Figure 12:
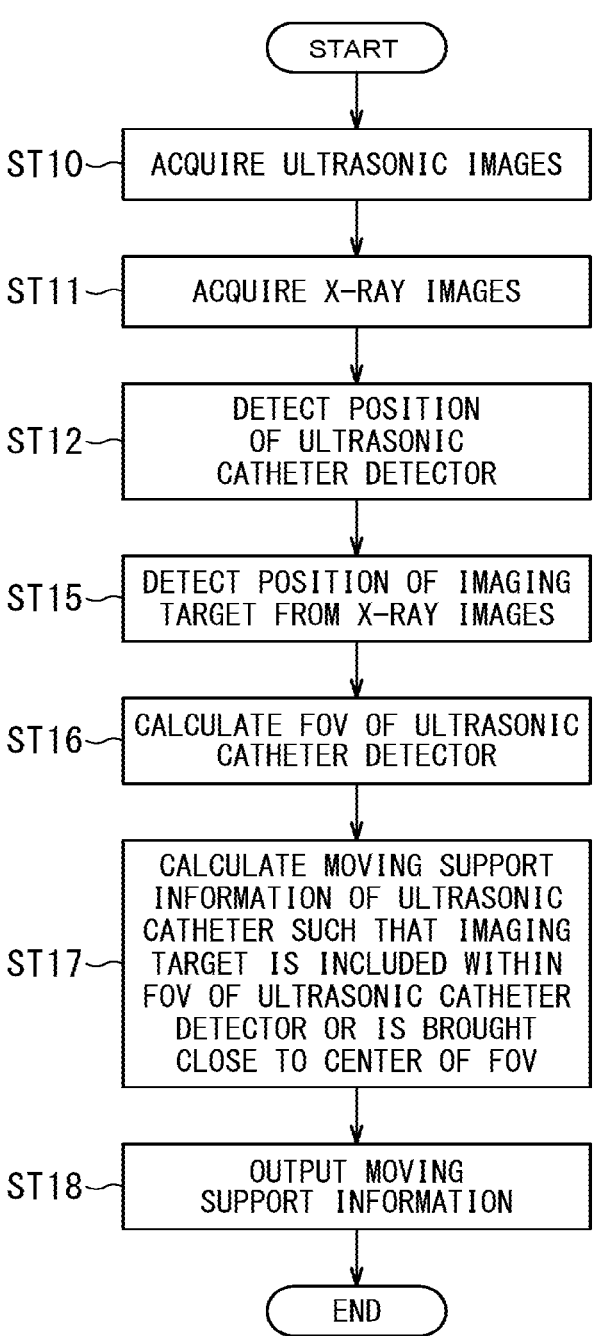
FIG. 12 is a flowchart illustrating processing to be executed by the medical image processing apparatus according to a first modification of the first embodiment.

FIG. 12 is a flowchart illustrating processing to be executed by the medical image processing apparatus and/or the medical image processing program according to the first modification of the first embodiment. As shown in FIG. 12, the step subsequent to the step ST12 may be the step 15 without executing the step ST13.

Second Embodiment

Figure 13:
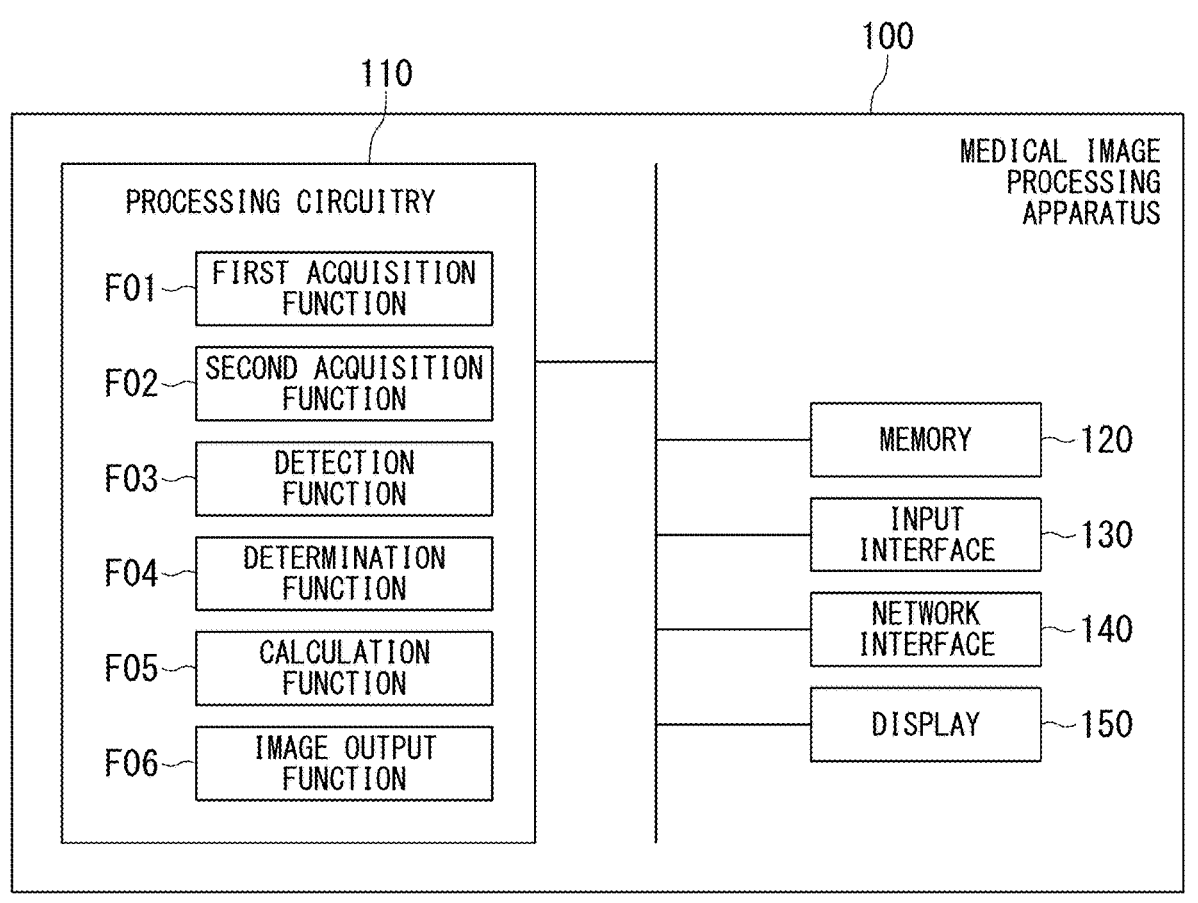
FIG. 13 is a schematic diagram illustrating a configuration of the medical image processing apparatus according to the second embodiment.

FIG. 13 illustrates a configuration of the medical image processing apparatus 100 according to the second embodiment. The difference between the second embodiment (FIG. 13) and the first embodiment (FIG. 7) is that the processing circuitry 110 of the medical image processing apparatus 100 shown in FIG. 13 further includes an image output function F06. The image output function F06 is a function to output ultrasonic images.

Figure 14:
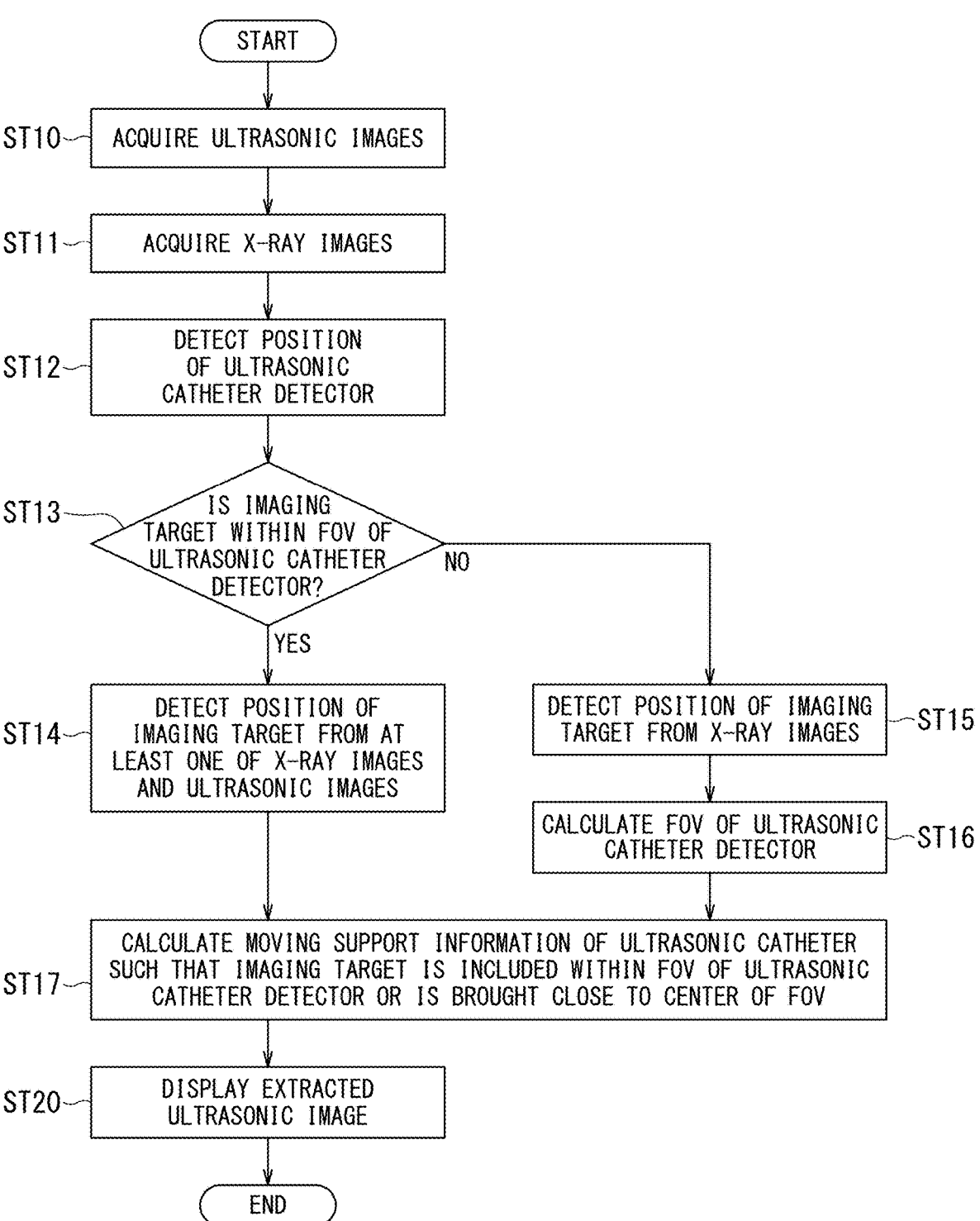
FIG. 14 is a flowchart illustrating processing to be executed by the medical image processing apparatus according to the second embodiment.

FIG. 14 is a flowchart illustrating processing to be executed by the medical image processing apparatus 100 and/or the medical image processing program according to the second embodiment. As shown in FIG. 14, the step ST20 is a step to be performed after the step ST18. In the step ST20, the ultrasonic image depicting part or all of the imaging target (which is at least one of the medical device 40 and the region of interest inside the body of the object P) is extracted from the plurality of ultrasonic images acquired in the step ST10, and the extracted ultrasonic image is outputted. The processing of outputting the ultrasonic image in the step ST20 is performed by the image output function F06.

As to the extraction method of the ultrasonic image in the step ST20, it is satisfactory if the image output function F06 outputs an ultrasonic image in which part or all of the imaging target including at least one of the medical device 40 and the region of interest inside the body of the object P is depicted. For example, from the viewpoint of outputting an ultrasonic image focused on the treatment target site, the ultrasonic image in the step ST20 may be an ultrasonic image in which both the treatment target site and the medical device are depicted.

Figure 15:
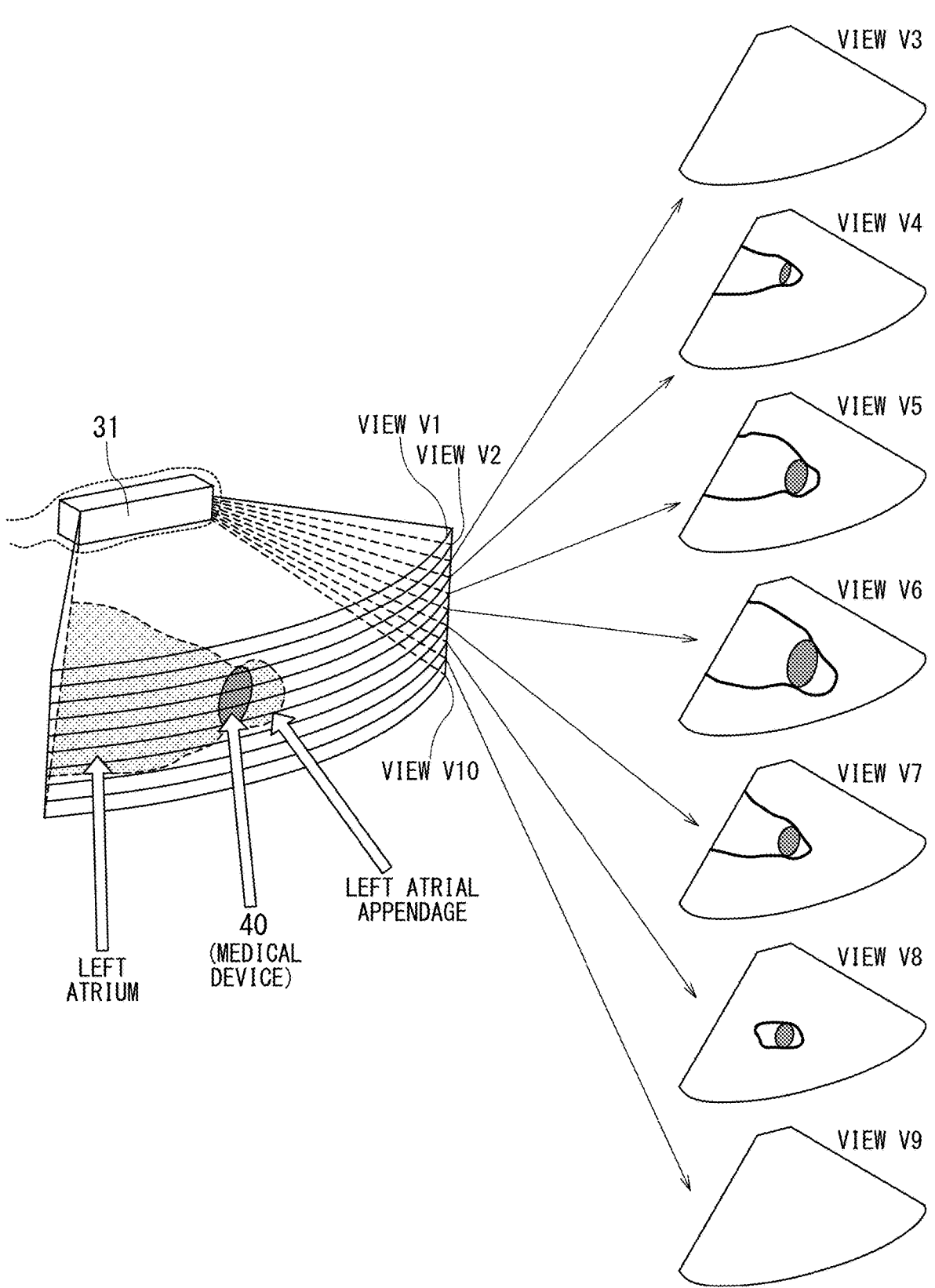
FIG. 15 is a schematic diagram illustrating ultrasonic images and its output order according to second embodiment.

FIG. 15 is a schematic diagram illustrating ultrasonic images and its output order according to second embodiment. In the case of the left atrial appendage closure procedure illustrated in FIG. 15, for example, when the ultrasonic images (i.e., the views V4 to V8) depicting both the left atrial appendage and the occlusion device (i.e., medical device 40) are selected as the ultrasonic images in the step ST20 from the FOV of the ultrasonic catheter 3 (i.e., set of all the views from the views V1 to V10 in FIG. 15), such selection facilitates observation intensively focused on the treatment target site, such as the state of contact between the left atrial appendage and the occlusion device.

Although the output order of the plurality of extracted ultrasonic images in the step ST20 is not limited to a specific order, the output order may be set so as to facilitate recognition of the conditions of the treatment target site. FIG. 15 also illustrates the output order of the ultrasonic images according to the second embodiment. The output order of the ultrasonic images may be the order of reciprocating from the ultrasonic image at one end of the range of the extracted view to the ultrasonic image at the opposite end. In the case of FIG. 15, for example, the ultrasonic images are repeatedly outputted in the order of the view V4, view V5, view V6, view V7, view V8, view V7, view V6, view V5, view V4, view V5 . . . .

Although the output can be started from any view, these views may be outputted by starting from the view near the center of the range to the view at one end of the range and back to the view at the opposite end of the range in a reciprocated manner. In the case of FIG. 15, for example, the ultrasonic images are repeatedly outputted in the order of the view V6, view V7, view V8, view V7, view V6, view V5, view V4, view V5, view V6, view V7, view V8, view V7 . . . .

Figure 16B:
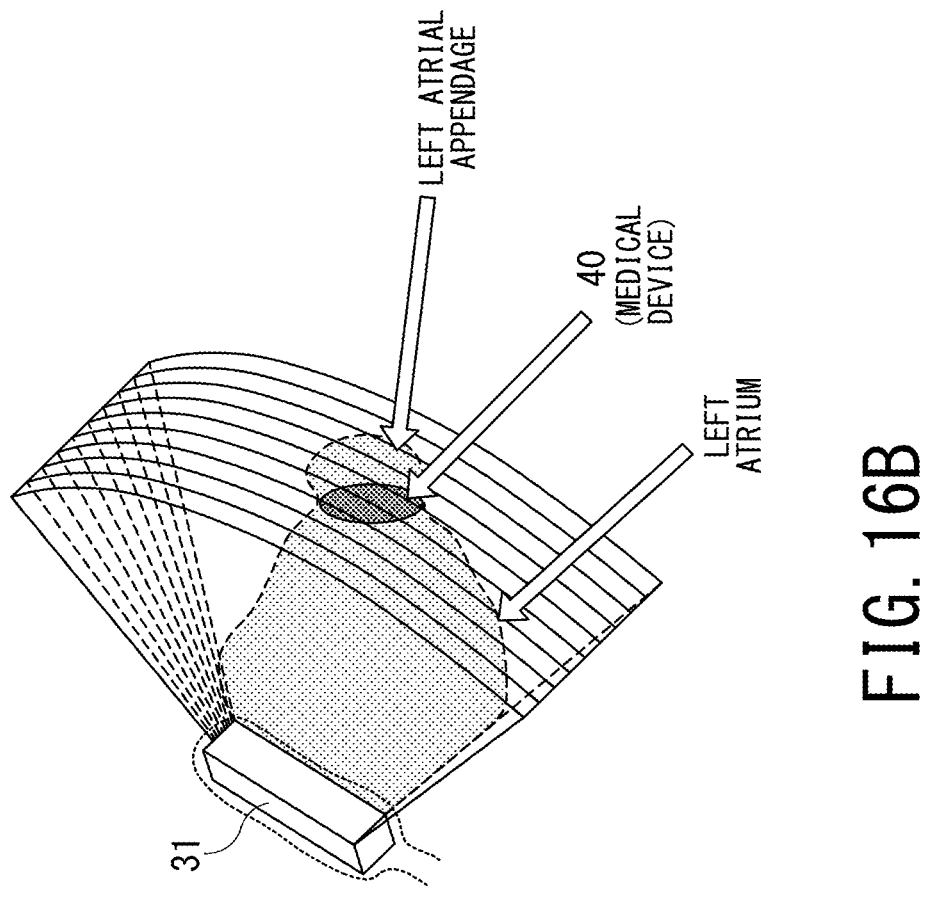
FIG. 16A and FIG. 16B are perspective views for illustrating movement support of the ultrasonic catheter based on ultrasonic images in the second embodiment, and respectively correspond to before and after the movement support.
Figure 16A:
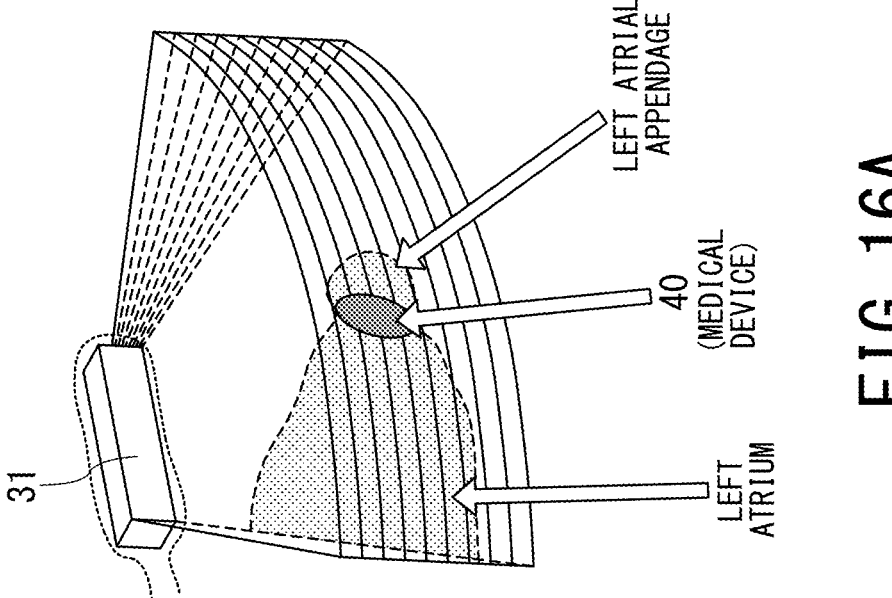

FIG. 16A and FIG. 16B are perspective views for illustrating the movement support of the ultrasonic catheter 3 based on ultrasonic images according to the second embodiment, and respectively correspond to before and after the movement support. FIG. 16A is the same as FIG. 15 and depicts a plurality of extracted ultrasonic images. As described above, the movement amount and moving direction of the ultrasonic catheter 3 and/or the angle of the array surface 31 of the detector 30 are preferably set as a value and direction that cause part or all of the imaging target (including at least one of the medical device 40 and the region of interest inside the body of the object P) to be maximally included within the FOV of the detector 30 of the ultrasonic catheter 3.

Thus, as shown in FIG. 16B, the moving support information for moving the ultrasonic catheter 3 may be calculated such that the imaging target is included within the FOV of the detector 30. Additionally, the moving support information for moving the ultrasonic catheter 3 may be calculated such that the imaging target is moved closer to the FOV of the detector 30. In this case, the moving support information is calculated by: extracting at least one ultrasonic image depicting part or all of the imaging target from the plurality of ultrasonic images acquired in the step ST10; and using the extracted ultrasonic image(s), for example.

The output of the ultrasonic images in the step ST20 may be performed by displaying them on the display 150 or may be performed by displaying them on at least one of the display 250 provided in the X-ray diagnostic apparatus 200 and the display 330 provided in the ultrasonic diagnostic apparatus 300.

For example, when the ultrasonic images depicting part or all of the medical device 40 are extracted and outputted, the burden of searching for the ultrasonic image(s) depicting the medical device 40 and the treatment target site on the manipulator is reduced. Further, observation of the target region during the medical treatment or the treatment process is facilitated by extracting and outputting the ultrasonic images that depict the region of interest inside the body of the object, for example.

Third Embodiment

Figure 17:
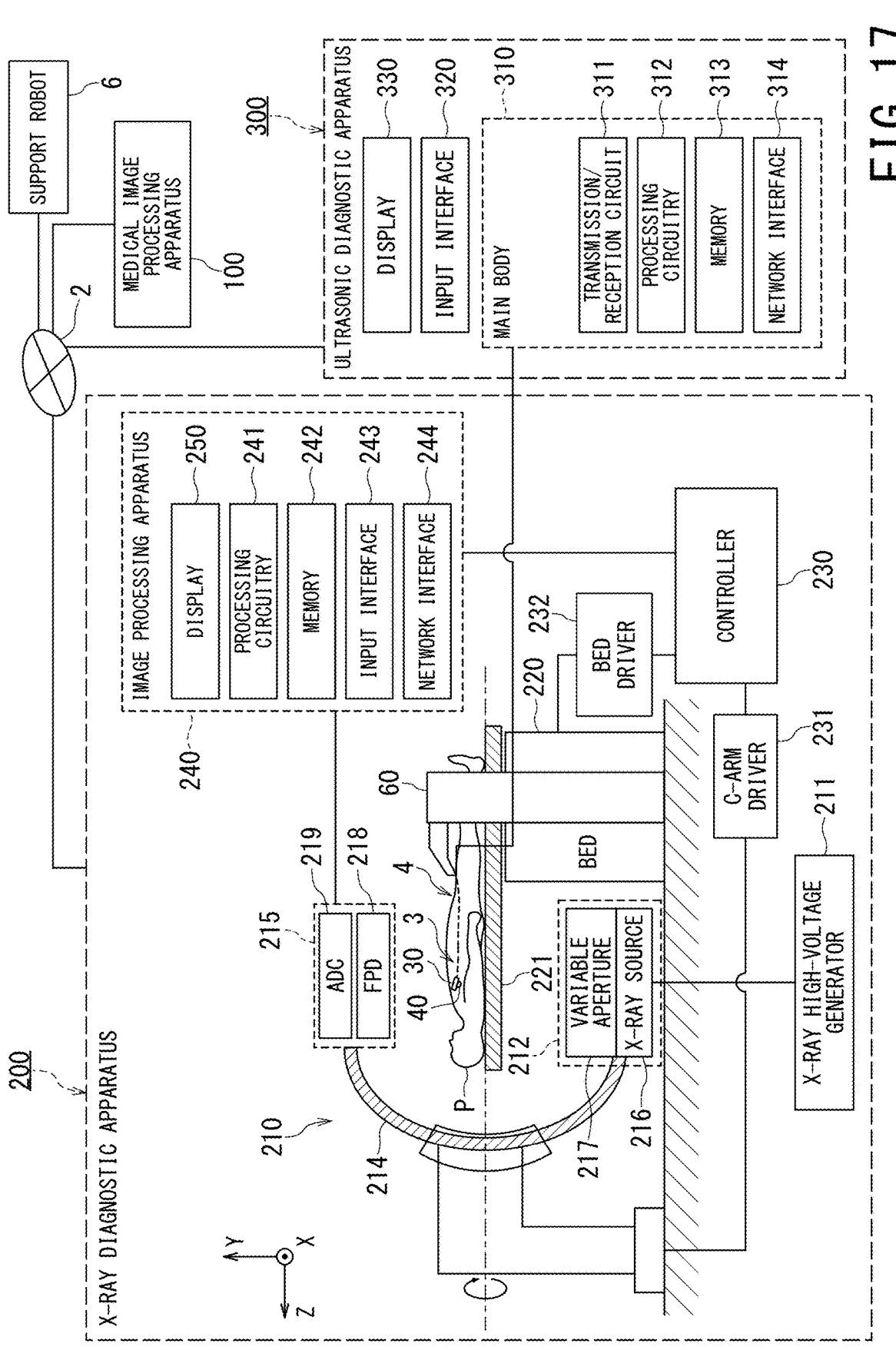
FIG. 17 is a schematic diagram illustrating a configuration of an X-ray diagnostic system provided with a support robot and the medical image processing apparatus according to the third embodiment.

FIG. 17 is a block diagram illustrating a configuration of the X-ray diagnostic system 1 provided with the medical image processing apparatus 100 according to the third embodiment. The medical image processing apparatus 100 according to the third embodiment has a function to control a support robot 6. The support robot 6 is an apparatus that can perform manipulation of inserting the ultrasonic catheter 3 and/or the manipulation catheter 4 into the body of the object P and advancing them to the treatment target site of the object P based on the user's instruction via a manipulation device (for example, a manipulation panel or a control console) installed at a remote location and/or control data from the remote location, for example.

As shown in FIG. 17, the support robot 6 has a robot main body 60 in addition to the manipulation device. The robot main body 60 is placed near the bed 220, inserts the ultrasonic catheter 3 and/or the manipulation catheter 4 into the body of the object P, and advances them to the treatment target site of the object P. The manipulation device for the support robot 6 may be disposed at a remote location different from the operating room or may be disposed inside the operating room.

Figure 18:
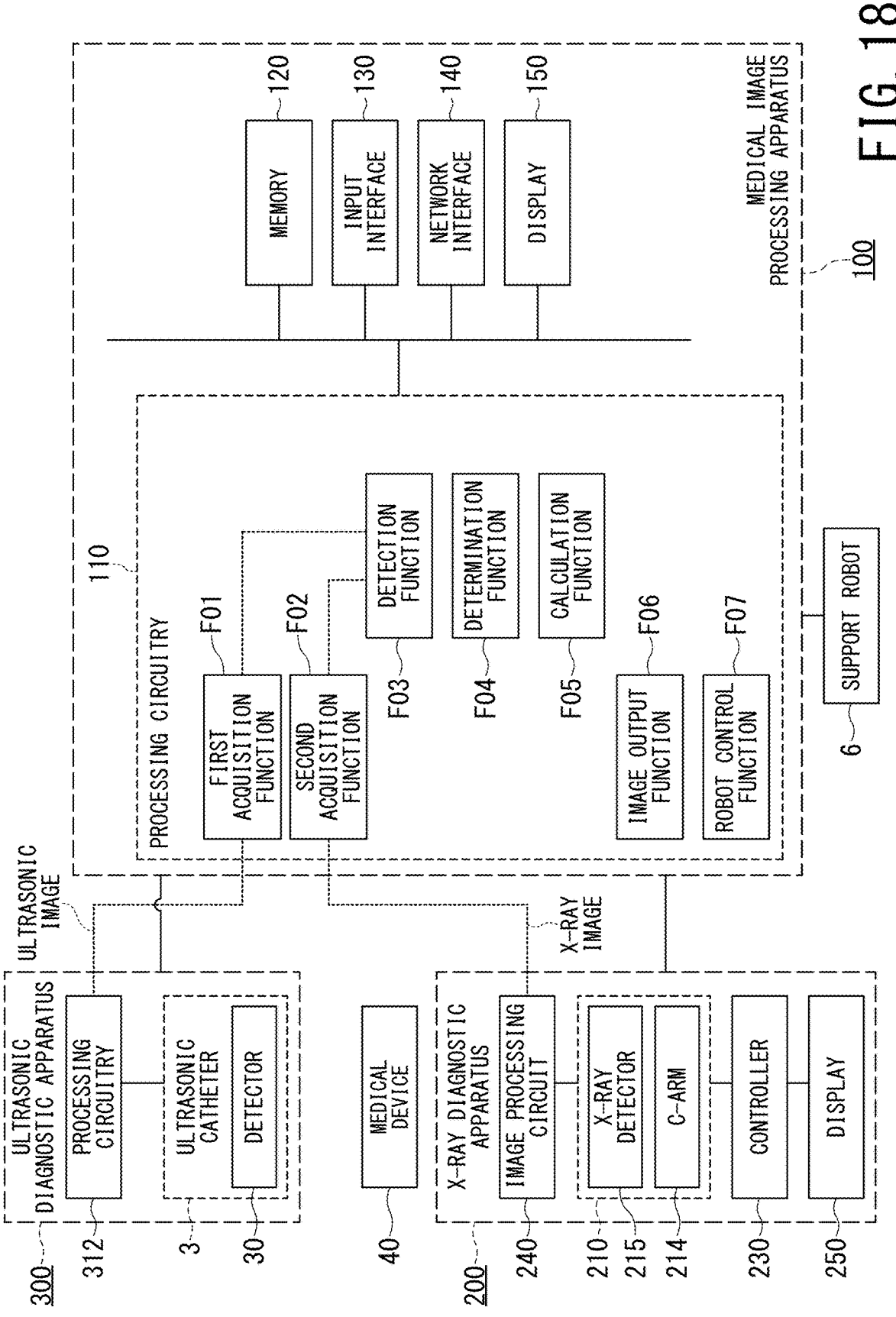
FIG. 18 is a schematic diagram illustrating a configuration of the medical image processing apparatus according to the third embodiment.

FIG. 18 illustrates a configuration of the medical image processing apparatus 100 according to the third embodiment. The difference from the first embodiment (FIG. 6) and the second embodiment (FIG. 13) is that the processing circuitry 110 of the medical image processing apparatus 100 according to the third embodiment further includes a robot control function F07. The robot control function F07 is a function to control motions of the support robot 6 by exchanging control data between the medical image processing apparatus 100, the X-ray diagnostic apparatus 200, and the support robot 6, which is a configuration separated from both apparatuses 100 and 200.

The robot control function F07 of the third embodiment converts the calculated moving support information of the ultrasonic catheter 3 into the control data for the support robot 6 and outputs the control data to the support robot 6. In this manner, the robot control function F07 controls the motions of the support robot 6 so as to move the ultrasonic catheter 3 based on the moving support information.

Further, the robot control function F07 may control the motions of the support robot 6 by: determining the moving speed of the ultrasonic catheter 3 appropriate for the tissue or organ of the object P at the tip of the ultrasonic catheter 3 based on the moving support information on the recommended route; moving the ultrasonic catheter 3 based on the determined moving speed; and/or moving the ultrasonic catheter 3 to bypass the tissue and/or organ of object P without contacting them. For example, in a moving organ such as the heart, the movement of the support robot 6 may be controlled so as to slow down the moving speed of the medical device 40.

According to at least one embodiment of the medical image processing device, the X-ray diagnostic system, and the non-transitory storage medium of a medical image processing program described above, the manipulator can be assisted in properly moving the ultrasonic catheter.

In the above-described embodiments, the term "processor" means a circuit such as a special-purpose or general-purpose CPU (Central Processing Unit), a GPU (Graphics Processing Unit), an ASIC (Application Specific Integrated Circuit), a programmable logic device including an SPLD (Simple Programmable Logic Device) and a CPLD (Complex Programmable Logic Device), and an FPGA (Field Programmable Gate Array), for example. When the processor is a CPU, for example, the processor implements various functions by reading in and executing the programs (the medical image processing program) stored in the memory. In addition, when the processor is an ASIC, for example, instead of storing the programs in the memory, the functions corresponding to the programs are directly incorporated as a logic circuit in the circuit of the processor. In this case, the processor implements the various functions by hardware processing in which the processor reads out and executes the programs incorporated in the circuit. Additionally or alternatively, the processor can implement the various functions by combining the software processing and the hardware processing.

Although a description has been given of the case where a single processor of the processing circuitry achieves the respective functions in the above-described embodiments, the processing circuitry may be configured by combining a plurality of independent processors so that each processor implements each function. Further, when a plurality of processors are provided, a memory for storing the programs may be provided for each processor or a single memory may collectively store the programs corresponding to the functions of all the processors.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the scope of the inventions as defined by the appended claims.

What is claimed is:

1. A medical image processing apparatus comprising processing circuitry configured to:

receive an ultrasonic image generated from a signal that is acquired by a detector of an ultrasonic catheter inserted into a body of an object;

receive an X-ray image in which the detector of the ultrasonic catheter and an imaging target are depicted, the imaging target being least one of a medical device inserted into the body of the object and a region of interest inside the body of the object;

determine the imaging target to be within a field of view (FOV) of the detector when the imaging target is depicted in the ultrasonic image;

determine the imaging target to be out of the FOV of the detector when the imaging target is not depicted in the ultrasonic image;

detect (a) a position of the detector of the ultrasonic catheter depicted in the X-ray image and (b) a position of the imaging target depicted in at least one of the ultrasonic image and the X-ray image;

detect, from the X-ray image, when the imaging target is not within the FOV of the detector, a position of a centroid of an array plane constituting the detector of the ultrasonic catheter and orientation of the array plane;

calculate the FOV of the detector from the position of the centroid of the array plane, a normal vector calculated from the orientation of the array plane, and a predetermined scanning range of the detector; and calculate moving support information that includes at least an angle of an array plane of the ultrasonic catheter based on the position of the detector of the ultrasonic catheter and the position of the imaging target, the moving support information being for moving the ultrasonic catheter in such a manner that the imaging target is included within the FOV of the detector or moved towards a center of the FOV of the detector.

2. The medical image processing apparatus according to claim 1, wherein, when the imaging target is within the FOV of the detector, the processing circuitry is further configured to detect the position of the imaging target within the FOV from the ultrasonic image and detect the position of the detector of the ultrasonic catheter from the X-ray image.

3. The medical image processing apparatus according to claim 1, wherein, when the imaging target is not within the FOV of the detector, the processing circuitry is further configured to detect the position of the detector of the ultrasonic catheter and the position of the imaging target from the X-ray image.

4. The medical image processing apparatus according to claim 1, wherein the moving support information to be calculated by the processing circuitry further includes at least one of: a movement amount of the ultrasonic catheter; a moving direction of the ultrasonic catheter; and information on a recommended-route of the ultrasonic catheter.

5. The medical image processing apparatus according to claim 1, further comprising a display configured to provide a user with the moving support information of the ultrasonic catheter.

6. The medical image processing apparatus according to claim 1, wherein the processing circuitry is further configured to control a support robot that supports manipulation of the ultrasonic catheter.

7. The medical image processing apparatus according to claim 5, wherein the processing circuitry is further configured to:

extract, from a plurality of ultrasonic images, an ultrasonic image in which part or all of the imaging target is depicted; and output an extracted ultrasonic image to the display.

8. The medical image processing apparatus according to claim 1, wherein the processing circuitry is further configured to:

extract, from a plurality of acquired ultrasonic images, an ultrasonic image in which part or all of the imaging target is depicted; and use an extracted ultrasound image to calculate the moving support information for moving the ultrasonic catheter in such a manner that the imaging target is included within the FOV of the detector or is moved closer to a center of the FOV of the detector.

9. The medical image processing apparatus according to claim 7, wherein the processing circuitry is further configured to output a plurality of extracted ultrasonic images:

in output order of reciprocating from an ultrasonic image at one end of an extracted range toward another ultrasonic image at an opposite end; or in reciprocating order between both ultrasonic images corresponding to both ends of the extracted range by starting from an ultrasonic image near the center of the extracted range.

10. The medical image processing apparatus according to claim 1, wherein the region of interest in the body of the object is a site where treatment, diagnosis, or support for a treatment process is performed.

11. An X-ray diagnostic system comprising: a medical image processing apparatus; and a network interface that can communicate with the medical image processing apparatus via a network, wherein the medical image processing apparatus includes processing circuitry configured to:

receive an ultrasonic image generated from a signal that is acquired by a detector of an ultrasonic catheter inserted into a body of an object;

receive an X-ray image in which the detector of the ultrasonic catheter and an imaging target are depicted, the imaging target being at least one of a medical device inserted into the body of the object and a region of interest inside the body of the object;

determine the imaging target to be within a field of view (FOV) of the detector when the imaging target is depicted in the ultrasonic image;

determine the imaging target to be out of the FOV of the detector when the imaging target is not depicted in the ultrasonic image;

detect (a) a position of the detector of the ultrasonic catheter depicted in the X-ray image and (b) a position of the imaging target depicted in at least one of the ultrasonic image and the X-ray image;

detect, from the X-ray image, a position of a centroid of an array plane constituting the detector of the ultrasonic catheter and orientation of the array plane;

calculate the FOV of the detector from the position of the centroid of the array plane, a normal vector calculated from the orientation of the array plane, and a predetermined scanning range of the detector; and calculate moving support information that includes at least an angle of an array plane of the ultrasonic catheter based on the position of the detector of the ultrasonic catheter and the position of the imaging target, the moving support information being for moving the ultrasonic catheter in such a manner that the imaging target is included within the FOV of the detector or moved towards a center of the FOV of the detector.

12. The X-ray diagnostic system according to claim 11, wherein the processing circuitry is further configured to control a support robot that supports manipulation of the ultrasonic catheter.

13. The X-ray diagnostic system according to claim 11, wherein, when the imaging target is within the FOV of the detector, the processing circuitry is further configured to detect the position of the imaging target within the FOV from the ultrasonic image and detect the position of the detector of the ultrasonic catheter from the X-ray image.

14. The X-ray diagnostic system according to claim 11, wherein, when the imaging target is not within the FOV of the detector, the processing circuitry is further configured to detect the position of the detector of the ultrasonic catheter and the position of the imaging target from the X-ray image.

15. A non-transitory computer-readable storage medium storing a medical image processing program for causing a computer to execute processing comprising:

receiving an ultrasonic image generated from a signal that is acquired by a detector of an ultrasonic catheter inserted into a body of an object;

receiving an X-ray image in which the detector of the ultrasonic catheter and an imaging target are depicted, the imaging target being least one of a medical device inserted into the body of the object and a region of interest inside the body of the object;

determining the imaging target to be within a field of view (FOV) of the detector when the imaging target is depicted in the ultrasonic image;

determining the imaging target to be out of the FOV of the detector when the imaging target is not depicted in the ultrasonic image;

detecting (a) a position of the detector of the ultrasonic catheter depicted in the X-ray image and (b) a position of the imaging target depicted in at least one of the ultrasonic image and the X-ray image;

detecting, from the X-ray image, when the imaging target is not within the FOV of the detector, a position of a centroid of an array plane constituting the detector of the ultrasonic catheter and orientation of the array plane;

calculating the FOV of the detector from the position of the centroid of the array plane, a normal vector calculated from the orientation of the array plane, and a predetermined scanning range of the detector; and calculating moving support information that includes at least an angle of an array plane of the ultrasonic catheter based on the position of the detector of the ultrasonic catheter and the position of the imaging target, the moving support information being for moving the ultrasonic catheter in such a manner that the imaging target is included within the FOV of the detector or moved towards a center of the FOV of the detector.

* * * * *